United States Patent
Cochrane et al.

(10) Patent No.: US 6,613,734 B2
(45) Date of Patent: *Sep. 2, 2003

(54) PEPTIDES-CONTAINING LIPOSOMAL SURFACTANTS

(75) Inventors: Charles G. Cochrane, La Jolla, CA (US); Susan D. Revak, San Diego, CA (US)

(73) Assignee: The Scripps Research Institute, La Jolla, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 08/488,123

(22) Filed: Jun. 7, 1995

(65) Prior Publication Data

US 2003/0099696 A1 May 29, 2003

Related U.S. Application Data

(63) Continuation-in-part of application No. 08/419,824, filed on Apr. 11, 1995, now Pat. No. 5,789,381, which is a continuation of application No. 08/060,833, filed on May 12, 1993, now Pat. No. 5,407,914, which is a continuation-in-part of application No. 07/715,397, filed on Jun. 14, 1991, now Pat. No. 5,260,273, which is a continuation-in-part of application No. 07/293,201, filed on Jan. 4, 1989, now Pat. No. 5,164,369, which is a continuation-in-part of application No. 07/141,200, filed on Jan. 6, 1988, now abandoned.

(51) Int. Cl.[7] .................. A61K 38/03; A61K 38/16
(52) U.S. Cl. .................. 514/2; 514/10; 514/11; 514/12; 514/13; 514/14; 424/450; 604/27; 604/54
(58) Field of Search .................. 574/2, 10, 11, 574/12, 13, 14; 424/450; 604/27, 54

(56) References Cited

U.S. PATENT DOCUMENTS

| | | | |
|---|---|---|---|
| 4,562,003 A | 12/1985 | Lewicki | 514/12 |
| 4,643,988 A | 2/1987 | Segrest | 514/13 |
| 4,656,253 A | 4/1987 | Lewicki | 514/11 |
| 4,705,684 A | 11/1987 | Beachey | 514/12 |
| 4,861,756 A * | 8/1989 | Jackson | 514/11 |
| 5,114,921 A * | 5/1992 | Zasloff | 514/12 |
| 5,164,369 A * | 11/1992 | Cochrane et al. | 514/12 |
| 5,260,273 A * | 11/1993 | Cochrane et al. | 514/12 |
| 5,407,914 A * | 4/1995 | Cochrane et al. | 514/12 |
| 5,409,898 A * | 4/1995 | Darveau et al. | 514/13 |
| 5,789,381 A * | 8/1998 | Cochrane et al. | |
| 6,013,619 A * | 1/2000 | Cochrane et al. | 514/2 |

FOREIGN PATENT DOCUMENTS

| | | |
|---|---|---|
| WO | WO 86/03408 | 6/1986 |
| WO | WO 87/06588 | 11/1987 |
| WO | WO 87/06943 | 11/1987 |
| WO | WO 88/03170 | 5/1988 |
| WO | WO 89/06657 | 7/1989 |
| WO | WO 92/22315 | 12/1992 |

OTHER PUBLICATIONS

STN file registry printout of "Leucine" RN 61-90-5.*
Evans, E. and Needham, D., "Physical Properties of Surfactant Bilayer Membranes: Thermal Transitions, Elasticity, Rigidity, Cohesion, and Colloidal Interactions," *J. Phys. Chem.* 91:4219-4228 (1987).
Kanellis, et al., "Studies of Synthetic Peptide Analogs of the Amphipathic Helix," *J. Biol. Chem.* 255:11464-11472 (1980).
Anantharamaiah, et al., "Synthetic Peptide Analogs of Apolipoproteins," *Proc. 9th Am. Pept. Symp.*:903-906 (1985).
Blanc, et al., *J. Biol. Chem.*, 258: 8277-8284 (1983).
Enhoring, *J. Appl. Physiol.*, 43: 198-203 (1977).
Glasser, et al., *PNAS USA 84*: 4007-4011 (1987).
Kaiser, et al., *PNAS USA, 80*: 1137-1143 (1983).
Kaiser, et al., *J. Biol Chem.*, 258: 8277-8284 (1983).
Notter, et al., *Chem. Abstracts 107*: 170948k (1987).
Ono, et al., *FEBS Letters 220*: 332-336 (1987).
Revak, et al., *Am. Rev. Respir. Dis.*, 134: 1258-1265 (1986).
Revak, et al., *J. Clin. Invest.*, 81: 826-833 (1988).
Ross, et al., *J. Biol. Chem.*, 261: 14283-14291 (1986).
Suzuki, et al., *Eur. J. Respir. Dis.*, 69: 336-345 (1986).
Whitsett, et al., *Chem. Abstracts*, 105: 94932s (1986).
Whitsett, et al., *Chem. Abstracts*, 105: 35325y (1986).
Yu, et al., *Chem. Abstracts*, 108: 68706p (1988).

* cited by examiner

*Primary Examiner*—Bennett Celsa
(74) *Attorney, Agent, or Firm*—Thomas E. Northrup; Thomas Fitting

(57) ABSTRACT

The present invention discloses useful surfactant molecules including polypeptides, proteins, and a variety of other organic molecules, as well as methods of making and using same. Surfactant compositions, including liposomal surfactant compositions, are also disclosed. In one preferred embodiment, a pulmonary surfactant composition comprises one or more pharmaceutically acceptable phospholipids admixed with a polypeptide comprising about 10 to 60 amino acid residues, wherein the polypeptide includes a sequence constituted by alternating groupings of charged amino acid residues and uncharged amino acid residues.

5 Claims, 8 Drawing Sheets

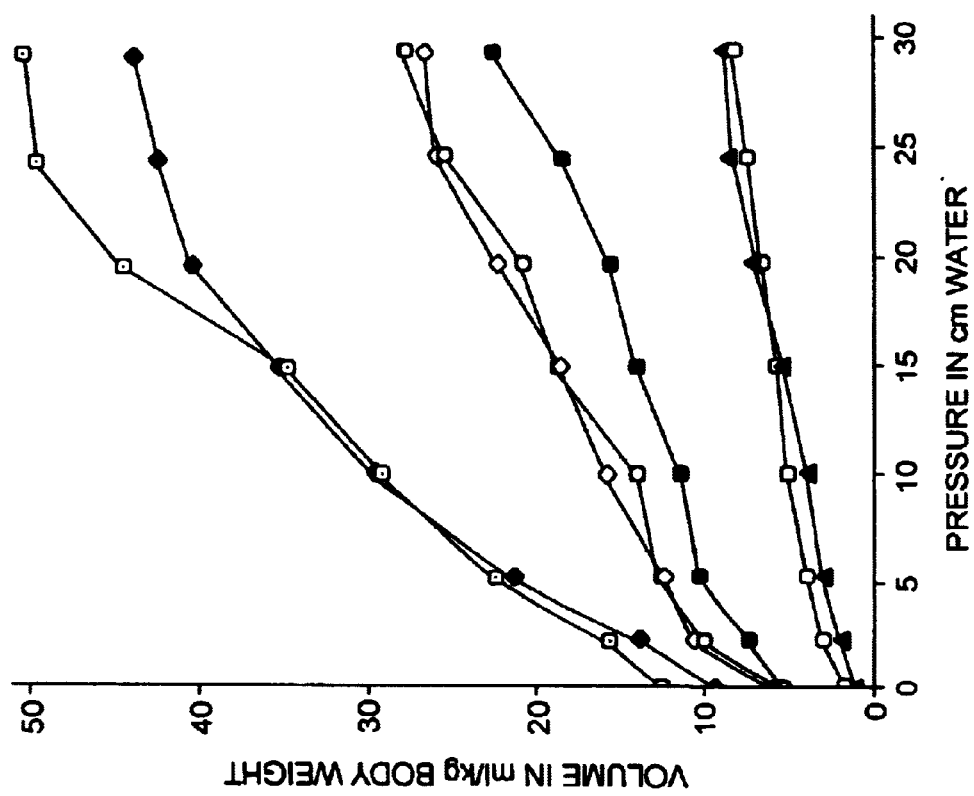
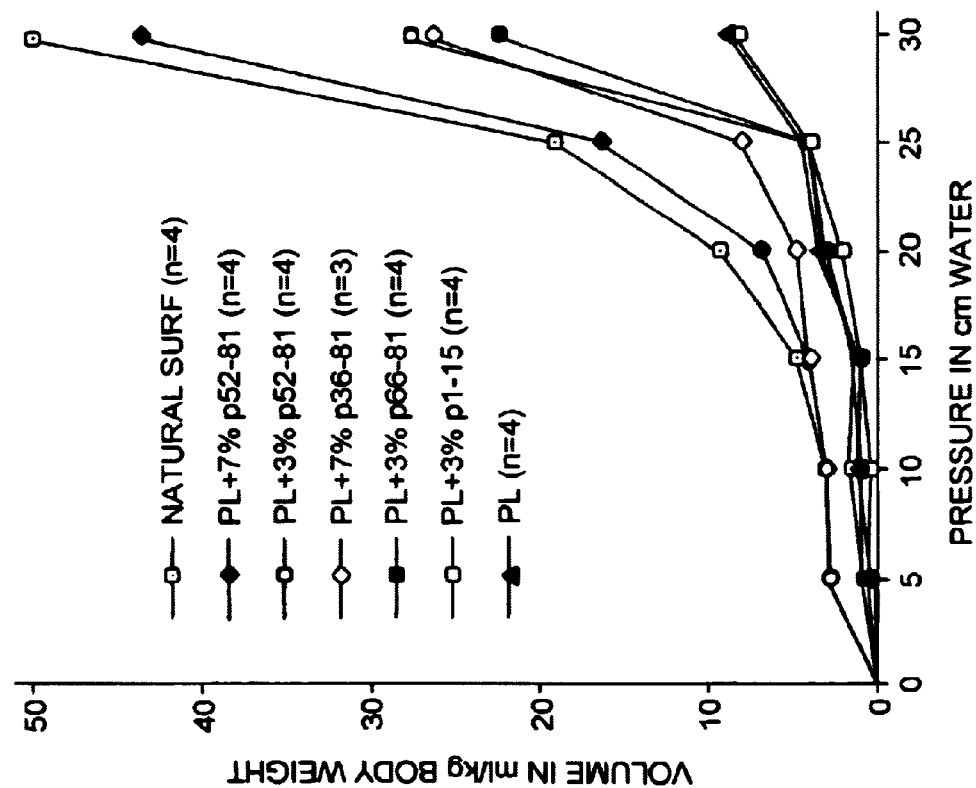
FIG. 2A
FIG. 2B

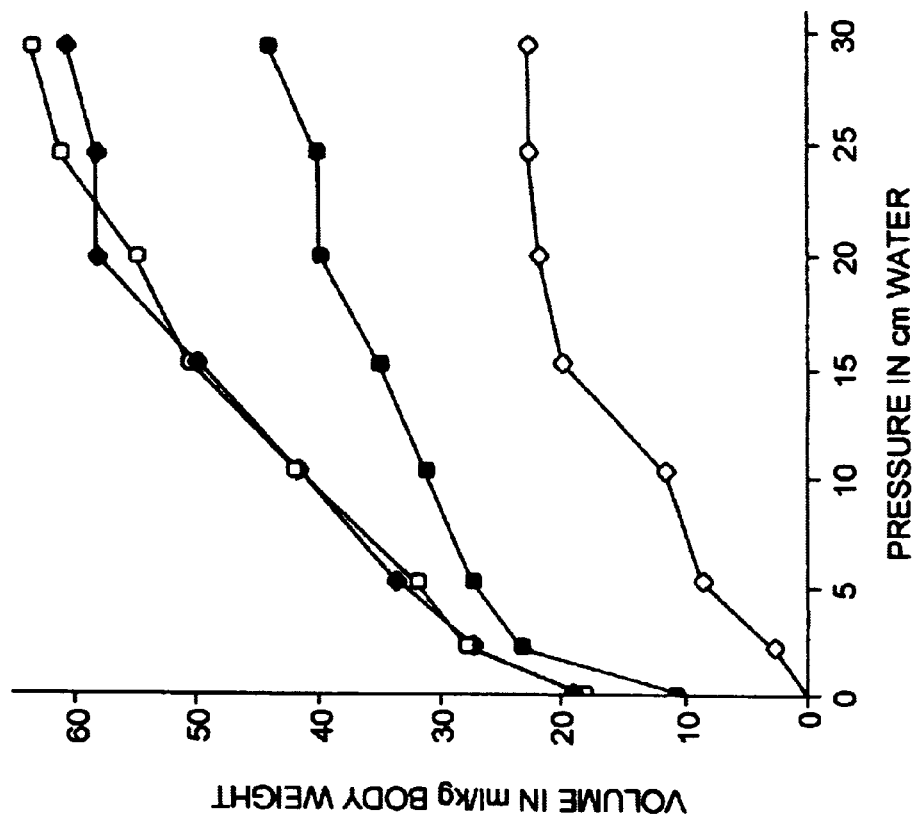
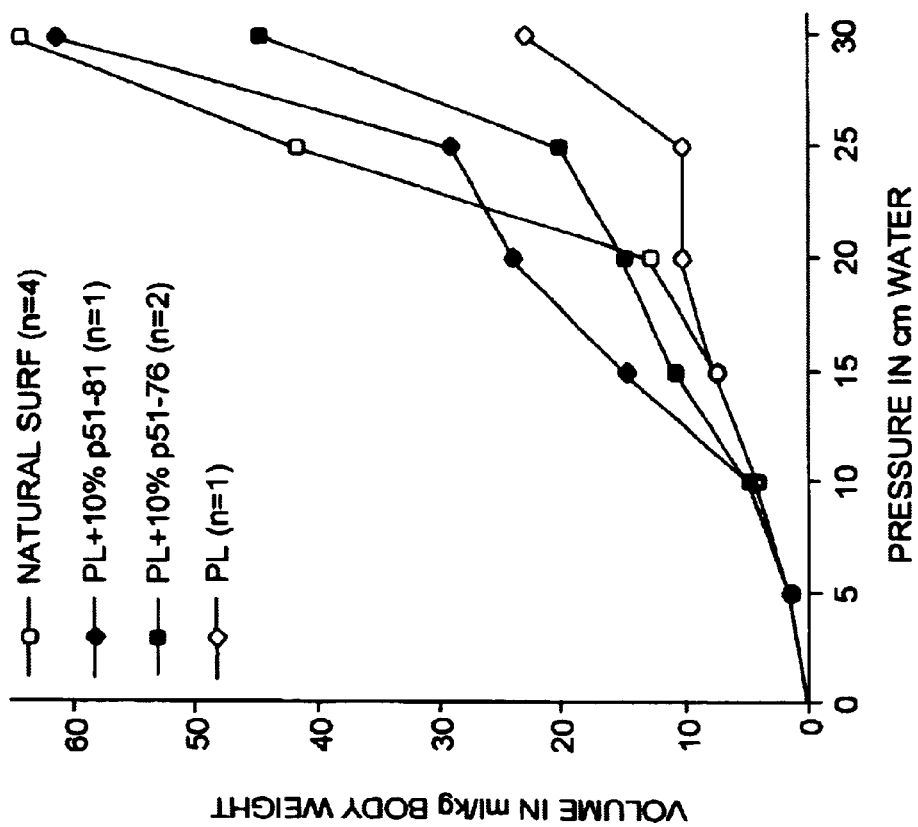

| | |
|---|---|
| CAC CTG GGC CTG TGC AAA TCC CGG CAG CCA GAG CCA GAG CAG GAG<br>His Leu Gly Leu Cys Lys Ser Arg Gln Pro Glu Pro Glu Gln Glu<br>-62 | 45 |
| CCA GGG ATG TCA GAC CCC CTG CCC AAA CCT CTG CGG GAC CCT CTG<br>Pro Gly Met Ser Asp Pro Leu Pro Lys Pro Leu Arg Asp Pro Leu | 90 |
| CCA GAC CCT CTG CTG GAC AAG CTC GTC GTC CCT GTG CTG CCC GGG<br>Pro Asp Pro Leu Leu Asp Lys Leu Val Val Pro Val Leu Pro Gly | 135 |
| GCC CTC CAG GCG AGG CCT GGG CCT CAC ACA CAG GAT CTC TCC GAG<br>Ala Leu Gln Ala Arg Pro Gly Pro His Thr Gln Asp Leu Ser Glu | 180 |
| CAG CAA TTC CCC ATT CCT CTC CCC TAT TGC TGG CTC TGC AGG GCT<br>Gln Gln Phe Pro Ile Pro Leu Pro Tyr Cys Trp Leu Cys Arg Ala<br>-1  1 | 225 |
| CTG ATC AAG CGG ATC CAA GCC ATG ATT CCC AAG GGT GCG CTA GCT<br>Leu Ile Lys Arg Ile Gln Ala Met Ile Pro Lys Gly Ala Leu Ala | 270 |
| GTG GCA GTG GCC CAG GTG TGC CGC GTG GTA CCT CTG GTG GCG GGC<br>Val Ala Val Ala Gln Val Cys Arg Val Val Pro Leu Val Ala Gly | 315 |
| GGC ATC TGC CAG TGC CTG GCT GAG CGC TAC TCC GTC ATC CTG CTC<br>Gly Ile Cys Gln Cys Leu Ala Glu Arg Tyr Ser Val Ile Leu Leu | 360 |
| GAC ACG CTG CTG GGC CGC ATG CTG CCC CAG CTG GTC TGC CGC CTC<br>Asp Thr Leu Leu Gly Arg Met Leu Pro Gln Leu Val Cys Arg Leu | 405 |
| GTC CTC CGG TGC TCC ATG GAT GAC AGC GCT GGC CCA AGG TCG CCG<br>Val Leu Arg Cys Ser Met Asp Asp Ser Ala Gly Pro Arg Ser Pro<br>81 | 450 |
| ACA GGA GAA TGG CTG CCG CGA GAC TCT GAG TGC CAC CTC TGC ATG<br>Thr Gly Glu Trp Leu Pro Arg Asp Ser Glu Cys His Leu Cys Met | 495 |
| TCC GTG ACC ACC CAG GCC GGG AAC AGC AGC GAG CAG GCC ATA CCA<br>Ser Val Thr Thr Gln Ala Gly Asn Ser Ser Glu Gln Ala Ile Pro<br>110 | 540 |
| CAG GCA ATG CTC CAG GCC TGT GTT GGC TCC TGG CTG GAC AGG GAA<br>Gln Ala Met Leu Gln Ala Cys Val Gly Ser Trp Leu Asp Arg Glu | 585 |
| AAG TGC AAG CAA TTT GTG GAG CAG CAC ACG CCC CAG CTG CTG ACC<br>Lys Cys Lys Gln Phe Val Glu Gln His Thr Pro Gln Leu Leu Thr | 630 |
| CTG GTG CCC AGG GGC TGG GAT GCC CAC ACC ACC TGC CAG GCC CTC<br>Leu Val Pro Arg Gly Trp Asp Ala His Thr Thr Cys Gln Ala Leu | 675 |
| GGA GTG TGT GGG ACC ATG TCC AGC CCT CTC CAG TGT ATC CAC AGC<br>Gly Val Cys Gly Thr Met Ser Ser Pro Leu Gln Cys Ile His Ser | 720 |
| CCC GAC CTT TGATGAGAAC TCAGCTGTCCA<br>Pro Asp Leu<br>181 | 750 |

FIG. 4

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO:1:

Lys Leu Leu Leu Leu Lys Leu Leu Leu Leu Lys Leu Leu Leu Leu Lys
1               5                   10                  15

Leu Leu Leu Leu Lys
            20

(2) INFORMATION FOR SEQ ID NO:2:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO:2:

Lys Leu Leu Leu Leu Leu Leu Leu Leu Lys Leu Leu Leu Leu Leu Leu
1               5                   10                  15

Leu Leu Lys Leu Leu
            20

(2) INFORMATION FOR SEQ ID NO:3:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO:3:

Lys Lys Leu Leu Leu Leu Leu Leu Leu Lys Lys Leu Leu Leu Leu Leu
1               5                   10                  15

Leu Leu Lys Lys Leu
            20

(2) INFORMATION FOR SEQ ID NO:4:

(i) SEQUENCE CHARACTERISTICS:

(A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO:4:

Asp Leu Leu Leu Leu Asp Leu Leu Leu Leu Asp Leu Leu Leu Leu Asp
1               5                   10                  15

Leu Leu Leu Leu Asp
            20

(2) INFORMATION FOR SEQ ID NO:5:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO:5

Arg Leu Leu Leu Leu Arg Leu Leu Leu Leu Arg Leu Leu Leu Leu Arg
1               5                   10                  15

Leu Leu Leu Leu Arg
            20

(2) INFORMATION FOR SEQ ID NO:6:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO:6:

Arg Leu Leu Leu Leu Leu Leu Leu Leu Arg Leu Leu Leu Leu Leu Leu
1               5                   10                  15

Leu Leu Arg Leu Leu
            20

(2) INFORMATION FOR SEQ ID NO:7:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO:7:

Arg Arg Leu Leu Leu Leu Leu Leu Leu Arg Arg Leu Leu Leu Leu Leu
1               5                   10                  15

Leu Leu Arg Arg Leu
            20

(2) INFORMATION FOR SEQ ID NO:8:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (xi) SEQUENCE DESCRIPTION: SEQ ID NO:8:

```
Arg Leu Leu Leu Leu Cys Leu Leu Leu Arg Leu Leu Leu Leu Cys Leu
1               5                   10                  15

Leu Leu Arg (2) INFORMATION FOR SEQ ID NO:9:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO:9:

Arg Leu Leu Leu Leu Cys Leu Leu Leu Arg Leu Leu Leu Leu Cys Leu
1               5                   10                  15

Leu Leu Arg Leu Leu
            20

(2) INFORMATION FOR SEQ ID NO:10:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (xi) SEQUENCE DESCRIPTION: SEQ ID NO:10:

Arg Leu Leu Leu Leu Cys Leu Leu Leu Arg Leu Leu Leu Leu Cys Leu
1               5                   10                  15

Leu Leu Arg Leu Leu Leu Cys Leu Leu Arg
            20                  25

(2) INFORMATION FOR SEQ ID NO:11:

(i) SEQUENCE CHARACTERISTICS:
        (A) LENGTH: 750 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: sig_peptide
        (B) LOCATION: 1..186

(ix) FEATURE:
        (A) NAME/KEY: CDS
        (B) LOCATION: 187..729

(xi) SEQUENCE DESCRIPTION: SEQ ID NO:11:

CACCTGGGCC TGTGCAAATC CCGGCAGCCA GAGCCAGAGC AGGAGCCAGG GATGTCAGAC      60

CCCCTGCCCA AACCTCTGCG GGACCCTCTG CCAGACCCTC TGCTGGACAA GCTCGTCGTC     120

CCTGTGCTGC CGGGGCCCT CCAGGCGAGG CCTGGGCCTC ACACACAGGA TCTCTCCGAG      180

CAGCAA TTC CCC ATT CCT CTC CCC TAT TGC TGG CTC TGC AGG GCT CTG        228
       Phe Pro Ile Pro Leu Pro Tyr Cys Trp Leu Cys Arg Ala Leu
        1               5                   10

ATC AAG CGG ATC CAA GCC ATG ATT CCC AAG GGT GCG CTA GCT GTG GCA       276
Ile Lys Arg Ile Gln Ala Met Ile Pro Lys Gly Ala Leu Ala Val Ala
15              20              25                  30

GTG GCC CAG GTG TGC CGC GTG GTA CCT CTG GTG GCG GGC GGC ATC TGC       324
Val Ala Gln Val Cys Arg Val Val Pro Leu Val Ala Gly Gly Ile Cys
```

-continued

```
                   35                  40                  45
CAG TGC CTG GCT GAG CGC TAC TCC GTC ATC CTG CTC GAC ACG CTG CTG       372
Gln Cys Leu Ala Glu Arg Tyr Ser Val Ile Leu Leu Asp Thr Leu Leu
                50                  55                  60

GGC CGC ATG CTG CCC CAG CTG GTC TGC CGC CTC GTC CTC CGG TGC TCC       420
Gly Arg Met Leu Pro Gln Leu Val Cys Arg Leu Val Leu Arg Cys Ser
            65                  70                  75

ATG GAT GAC AGC GCT GGC CCA AGG TCG CCG ACA GGA GAA TGG CTG CCG       468
Met Asp Asp Ser Ala Gly Pro Arg Ser Pro Thr Gly Glu Trp Leu Pro
        80                  85                  90

CGA GAC TCT GAG TGC CAC CTC TGC ATG TCC GTG ACC ACC CAG GCC GGG       516
Arg Asp Ser Glu Cys His Leu Cys Met Ser Val Thr Thr Gln Ala Gly
95                  100                 105                 110

AAC AGC AGC GAG CAG GCC ATA CCA CAG GCA ATG CTC CAG GCC TGT GTT       564
Asn Ser Ser Glu Gln Ala Ile Pro Gln Ala Met Leu Gln Ala Cys Val
                115                 120                 125

GGC TCC TGG CTG GAC AGG GAA AAG TGC AAG CAA TTT GTG GAG CAG CAC       612
Gly Ser Trp Leu Asp Arg Glu Lys Cys Lys Gln Phe Val Glu Gln His
                130                 135                 140

ACG CCC CAG CTG CTG ACC CTG GTG CCC AGG GGC TGG GAT GCC CAC ACC       660
Thr Pro Gln Leu Leu Thr Leu Val Pro Arg Gly Trp Asp Ala His Thr
            145                 150                 155

ACC TGC CAG GCC CTC GGA GTG TGT GGG ACC ATG TCC AGC CCT CTC CAG       708
Thr Cys Gln Ala Leu Gly Val Cys Gly Thr Met Ser Ser Pro Leu Gln
        160                 165                 170

TGT ATC CAC AGC CCC GAC CTT TGATGAGAAC TCAGCTGTCC A                   750
Cys Ile His Ser Pro Asp Leu
175                 180
```

(2) INFORMATION FOR SEQ ID NO:12:

(i) SEQUENCE CHARACTERISTICS:
        (A) LENGTH: 181 amino acids
        (B) TYPE: amino acid
        (D) TOPOLOGY: linear (ii) MOLECULE TYPE: protein (xi) SEQUENCE DESCRIPTION: SEQ ID NO:12:

```
Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
                20                  25                  30

Gln Val Cys Arg Val Val Pro Leu Val Ala Gly Gly Ile Cys Gln Cys
            35                  40                  45

Leu Ala Glu Arg Tyr Ser Val Ile Leu Leu Asp Thr Leu Leu Gly Arg
        50                  55                  60

Met Leu Pro Gln Leu Val Cys Arg Leu Val Leu Arg Cys Ser Met Asp
65                  70                  75                  80

Asp Ser Ala Gly Pro Arg Ser Pro Thr Gly Glu Trp Leu Pro Arg Asp
                85                  90                  95

Ser Glu Cys His Leu Cys Met Ser Val Thr Thr Gln Ala Gly Asn Ser
            100                 105                 110

Ser Glu Gln Ala Ile Pro Gln Ala Met Leu Gln Ala Cys Val Gly Ser
        115                 120                 125

Trp Leu Asp Arg Glu Lys Cys Lys Gln Phe Val Glu Gln His Thr Pro
    130                 135                 140

Gln Leu Leu Thr Leu Val Pro Arg Gly Trp Asp Ala His Thr Thr Cys
145                 150                 155                 160
```

```
Gln Ala Leu Gly Val Cys Gly Thr Met Ser Ser Pro Leu Gln Cys Ile
            165                 170                 175
His Ser Pro Asp Leu
            180

(2) INFORMATION FOR SEQ ID NO:13:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO:13:

His Leu Leu Leu Leu His Leu Leu Leu Leu His Leu Leu Leu Leu His
1               5                   10                  15

Leu Leu Leu Leu His
            20
```

PEPTIDES-CONTAINING LIPOSOMAL SURFACTANTS

CROSS REFERENCE TO RELATED APPLICATIONS

This is a continuation-in-part of application Ser. No. 08/419,824, filed Apr. 11, 1995 (now U.S. Pat. No. 5,789,381), which is a continuation of application Ser. No. 08/060,833, filed May 12, 1993 (now U.S. Pat. No. 5,407,914), which is a continuation-in-part of application Ser. No. 07/715,397, filed Jun. 14, 1991 (now U.S. Pat. No. 5,260,273), which is a continuation-in-part of application Ser. No. 07/293,201, filed Jan. 4, 1989 (now U.S. Pat. No. 5,164,369), which is a continuation-in-part of application Ser. No. 07/141,200, filed Jan. 6, 1988 (now abandoned). The disclosures of the foregoing applications are hereby incorporated by reference herein.

This invention was made with government support under contract No. HL 23584 and GM 37696 from the NIH and N00014 from the Office of Naval Research.

TECHNICAL FIELD

The present invention relates to surfactant molecules, including polypeptides, proteins, and a variety of other organic molecules, which are suitable for use in the treatment of respiratory distress syndrome in infants as well as in adults.

BACKGROUND

Naturally-occurring pulmonary surfactant is a complex mixture of lipids and proteins that promotes the formation of a monolayer at the alveolar air-water interface and, by reducing the surface tension, prevents collapse of the alveolus during expiration. Premature infants, and occasionally full term neonates, may lack sufficient endogenous surfactant for normal lung function. This can give rise to a condition termed respiratory distress syndrome (RDS) which may necessitate mechanical ventilation and administration of hyperbaric oxygen. Such intervention, unfortunately, can produce permanent damage to lung tissue and may cause retinopathy of prematurity (ROP) leading to blindness.

Pulmonary surfactant (PS) lines the alveolar epithelium of mature mammalian lungs. Natural PS has been described as a "lipoprotein complex" because it contains both phospholipids and apoproteins that interact to reduce surface tension at the lung air-liquid interface. Natural surfactant contains several lipid species of which dipalmitoyl phosphatidylcholine (DPPC) is the major component together with phosphatidylglycerol (PG) and palmitic acid (PA). At least three specific proteins are also associated, termed SP-A, SP-B and SP-C. Of these three, SP-B and SP-C are distinct, low molecular weight, relatively hydrophobic proteins that have been shown to enhance the surface-active properties of surfactant phospholipid mixtures. It is believed that they facilitate transfer of lipids from the bulk phase lamellar organization to the air-water interface and also stabilize the lipid monolayer during expiration. The structure of SP-B (which is alternatively referred to as SP18) is unusual in that charged amino acids (predominantly basic) are located at fairly regular intervals within stretches of otherwise hydrophobic residues. For the domain consisting of residues 59–80 of the native SP-B sequence, these charged groups have been shown to be necessary for biological activity. In addition, natural and synthetic peptides which are modeled on this hydrophobic-hydrophilic domain when combined with DPPC and PG exhibit good surfactant activity.

Surfactant is stored in lung epithelial cells in the form of lamellar bodies and, following export, it undergoes a structural transition to form tubular myelin before giving rise to a monolayer at the air-water interface. It has been proposed that surfactant proteins SP-A, -B and -C may facilitate these structural transitions and stabilize the lipid monolayer during expansion and contraction of the alveolus; however, an understanding of lipid-protein interactions at the molecular level is presently lacking. The present invention, therefore, has important implications not only with respect to the treatment of RDS in infants as well as adults, but also because of the insight it may provide into lipid-protein interactions in general.

Several exogenous surfactant formulations are currently used in the treatment of infant RDS. While these have reduced morbidity and mortality, continual improvements are needed. In particular, because of the complications that can arise due to mechanical ventilation and administration of hyperbaric oxygen, the sooner normal lung function can be established in a premature infant the more favorable will be the clinical outcome.

Consistent with the foregoing, important characteristics in an exogenous surfactant include the ability to spread rapidly to the alveoli following administration and the ability to maintain a stable monolayer at the alveolar air-water interface so that repeated treatment was not required. The within-disclosed compounds and compositions are believed useful in the preparation of superior exogenous surfactants.

SUMMARY

The present invention discloses a wide variety of surfactant molecules which may be formulated, prepared and utilized as disclosed herein. In various preferred embodiments of the present invention, it is contemplated that the surfactant molecules comprise dipeptides, larger polypeptides, or proteins. In other preferred embodiments, surfactant molecules comprise a variety of organic molecules, including L-amino acids, D-amino acids, substituted amino acids (e.g., amino acids with modified R groups), amino acid metabolites and catabolites, molecules with "designed" side chains, and amino acid mimics or analogs. Molecules comprising dipeptides or polypeptides joined by linkages other than peptide bonds are also encompassed by the present invention; indeed, any organic molecule possessing or exhibiting surfactant activity as described herein is a "surfactant molecule" as contemplated by the present invention.

Therefore, in various preferred embodiments of the present invention, a wide variety of surfactant polypeptides is disclosed. In one embodiment, a preferred polypeptide comprises at least about 4, and more preferably at least about 10, amino acid residues and no more than about 60 amino acid residues and is constituted by alternating groupings of charged amino acid residues and uncharged amino acid residues such that the polypeptide, when admixed with a pharmaceutically acceptable phospholipid, forms a pulmonary surfactant having a surfactant activity greater than the surfactant activity of the phospholipid alone.

In one preferred embodiment, a surfactant polypeptide comprises at least 10 amino acid residues and no more than about 60 amino acid residues and is constituted by alternating groupings of charged amino acid residues and uncharged amino acid residues as represented by the formula $[(\text{Charged})_a(\text{Uncharged})_b]_c(\text{Charged})_d$, wherein a has an average value of about 1 to about 5; b has an average value of about 3 to about 20; c is 1 to 10; and d is 0 to 3. It is further preferred that the polypeptide, when admixed with a pharmaceutically acceptable phospholipid, forms a pulmonary surfactant having a surfactant activity greater than the surfactant activity of the phospholipid alone.

In another preferred embodiment, the present invention discloses polypeptides including a sequence having alternating groupings of amino acid residues as represented by the formula $(Z_aJ_b)_cZ_d$, wherein Z is an amino acid residue independently selected from the group consisting of R, D, E, and K; J is an α-aminoaliphatic carboxylic acid; a has an average value of about 1 to about 5; b has an average value of about 3 to about 20; c is 1 to 10; and d is 0 to 3.

In yet another preferred embodiment, surfactant polypeptides are disclosed which have alternating groupings of amino acids residue regions as represented by the formula $(B_aU_b)_cB_d$, wherein B is an amino acid residue independently selected from the group consisting of H, 5-hydroxylysine, 4-hydroxyproline, and 3-hydroxyproline; U is an amino acid residue independently selected from the group consisting of V, I, L, C, Y, and F; a has an average value of about 1 to about 5; b has an average value of about 3 to about 20; c is 1 to 10; and d is 0 to 3. In another preferred variation, B is an amino acid derived from collagen and is preferably selected from the group consisting of 5-hydroxylysine, 4-hydroxyproline, and 3-hydroxyproline.

Another preferred embodiment of the present invention discloses polypeptides including a sequence having alternating groupings of amino acid residues as represented by the formula $(B_aJ_b)_cB_d$, wherein B is an amino acid residue independently selected from the group consisting of H, 5-hydroxylysine, 4-hydroxyproline, and 3-hydroxyproline; J is an α-aminoaliphatic carboxylic acid; a has an average value of about 1 to about 5; b has an average value of about 3 to about 20; c is 1 to 10; and d is 0 to 3. In one preferred variation, J is an α-aminoaliphatic carboxylic acid having four to six carbons, inclusive. In another preferred variation, J is an α-aminoaliphatic carboxylic acid having six or more carbons, inclusive. In yet another variation, J is preferably selected from the group consisting of α-aminobutanoic acid, α-aminopentanoic acid, α-amino-2-methylpropanoic acid, and α-aminohexanoic acid.

A further preferred embodiment of the present invention discloses polypeptides including a sequence having alternating groupings of amino acid residues as represented by the formula $(Z_aU_b)_cZ_d$, wherein Z is an amino acid residue independently selected from the group consisting of R, D, E, and K; U is an amino acid residue independently selected from the group consisting of V, I, L, C, Y and F; a has an average value of about 1 to about 5; b has an average value of about 3 to about 20; c is 1 to 10; and d is 0 to 3.

The present invention also contemplates a variety of surfactant compositions, particularly liposomal surfactants. Thus, in one preferred embodiment, the invention discloses a liposomal surfactant composition prepared from a polypeptide comprising about 10 amino acid residues and no more than about 60 amino acid residues and is constituted by alternating groupings of charged amino acid residues and uncharged amino acid residues, and a pharmaceutically acceptable phospholipid, wherein the polypeptide is present in an amount sufficient to increase the surfactant activity of the composition above that of the phospholipid.

In another preferred variation, a surfactant composition of the present invention comprises a surfactant molecule constituted by alternating groupings of charged and uncharged residues; the residues may be amino acids, modified amino acids, amino acid analogs or derivatives, and the like. Molecules having surfactant activity as disclosed herein are especially preferred for use in compositions of the present invention.

In one preferred variation, a surfactant composition of the present invention includes a polypeptide comprising at least 10 amino acid residues and no more than about 60 amino acid residues constituted by alternating groupings of charged amino acid residues and uncharged amino acid residues as represented by the formula $[(\text{Charged})_a(\text{Uncharged})_b]_c(\text{Charged})_d$, wherein a has an average value of about 1 to about 5; b has an average value of about 3 to about 20; c is 1 to 10; and d is 0 to 3.

In another preferred embodiment, a surfactant composition comprises a polypeptide including a sequence having alternating groupings of amino acid residues as represented by the formula $(Z_aJ_b)_cZ_d$, wherein Z is an amino acid residue independently selected from the group consisting of R, D, E, and K; J is an α-aminoaliphatic carboxylic acid; a has an average value of about 1 to about 5; b has an average value of about 3 to about 20; c is 1 to 10; and d is 0 to 3.

In yet another preferred embodiment, a surfactant composition comprises a surfactant polypeptide including a sequence having alternating groupings of amino acid residue regions as represented by the formula $(B_aU_b)_cB_d$, wherein B is an amino acid residue independently selected from the group consisting of H, 5-hydroxylysine, 4-hydroxyproline, and 3-hydroxyproline; U is an amino acid residue independently selected from the group consisting of V, I, L, C, Y, and F; a has an average value of about 1 to about 5; b has an average value of about 3 to about 20; c is 1 to 10; and d is 0 to 3.

Another preferred embodiment of the present invention discloses compositions comprising polypeptides including a sequence having alternating groupings of amino acid residues as represented by the formula $(B_aJ_b)_cB_d$, wherein B is an amino acid residue independently selected from the group consisting of H, 5-hydroxylysine, 4-hydroxyproline, and 3-hydroxyproline; J is an α-aminoaliphatic carboxylic acid; a has an average value of about 1 to about 5; b has an average value of about 3 to about 20; c is 1 to 10; and d is 0 to 3. In one preferred variation, J is an α-aminoaliphatic carboxylic acid having four to six carbons, inclusive. In another variation, J is preferably selected from the group consisting of α-aminobutanoic acid, α-aminopentanoic acid, α-amino-2-methylpropanoic acid, and α-aminohexanoic acid.

A further preferred embodiment of the present invention discloses compositions comprising polypeptides including a sequence having alternating groupings of amino acid residues as represented by the formula $(Z_aU_b)_cZ_d$, wherein Z is an amino acid residue independently selected from the group consisting of R, D, E, and K; U is an amino acid residue independently selected from the group consisting of V, I, L, C, Y and F; a has an average value of about 1 to about 5; b has an average value of about 3 to about 20; c is 1 to 10; and d is 0 to 3.

In various preferred embodiments of the present invention, as noted previously, surfactant compositions also comprise one or more phospholipids, wherein the phospholipid is present in the range of about 50–100 weight percent. The polypeptide:phospholipid weight ratio is in the range of about 1:7 to about 1:1,000 in various preferred surfactant compositions of the present invention. Suitable phospholipids are preferably selected from the following group: 1,2- dipalmitoyl-sn-glycero-3-phosphocholine (dipalmitoylphosphatidylcholine, DPPC); phosphatidyl glycerol (PG); and an admixture of DPPC and PG in a weight ratio of about 3:1.

The surfactant compositions (e.g., liposomal surfactants) of the present invention may further comprise palmitic acid, in various preferred embodiments. Preferably, the phospholipid comprises about 50–90 weight percent and the palmitic acid comprises the remaining 10–50 weight percent of the lipid portion of the surfactant. As in other preferred embodiments, the phospholipid may be selected from the group consisting of 1,2-dipalmitoyl-sn-glycero-3-phosphocholine (dipalmitoylphosphatidylcholine, DPPC); phosphatidyl glycerol (PG); and an admixture of DPPC and PG. If an admixture of DPPC and PG is selected, it is preferable that DPPC and PG be present in a weight ratio of about 3:1.

The present invention also discloses preferred methods of treating respiratory distress syndrome in patients of any age, including neonates and adults. One such method comprises administering to a patient in need of such treatment a therapeutically effective amount of a surfactant composition—preferably, a liposomal surfactant composition—prepared from a polypeptide (or other surfactant molecule) of the present invention and a pharmaceutically acceptable phospholipid, wherein the polypeptide is combined with the phospholipid in an amount sufficient to increase the surfactant activity of the composition above that of the phospholipid. The present invention also discloses a method of treating respiratory distress syndrome wherein the polypeptide is constituted by at about 10–60 amino acid residues and constituted by alternating groupings of charged amino acid residues and uncharged amino acid residues as represented by the formula $[(\text{Charged})_a(\text{Uncharged})_b]_c(\text{Charged})_d$, wherein a has an average value of about 1 to about 5; b has an average value of about 3 to about 20; c is 1 to 10; and d is 0 to 3. In various preferred embodiments, such a polypeptide, when admixed with a pharmaceutically acceptable phospholipid, forms a pulmonary surfactant having a surfactant activity greater than the surfactant activity of the phospholipid alone.

A wide variety of surfactant molecules, proteins, and polypeptides which are preferred for use according to the disclosed methods are described above and in the sections that follow. Other preferred components of surfactant compositions used as disclosed herein include a variety of phospholipids and palmitic acid, as further described herein.

BRIEF DESCRIPTION OF THE DRAWINGS

FIGS. 2A and 2B are two graphs that illustrate the results of a static compliance study of exemplary surfactants of this invention using the fetal rabbit model previously described in Revak, et al, *Am. Rev. Respir. Dis.* 134: 1258–1256 (1986). Following instillation of a surfactant or control (e.g. phospholipid) into the trachea, the rabbit was ventilated for 30 minutes prior to making static compliance measurements. The "x" axis represents the pressure in cm of water, while the "y" axis represents the volume in ml/kg of body weight. The graph in FIG. 2A represents values at inflation and the graph on the right (FIG. 2B) represents deflation values. The results for the following tested surfactants are illustrated: natural surfactant (open square with a dot in the center), phospholipid (PL) with 7% p52–81(a polypeptide corresponding to residues 52 to 81 of SP18) (closed diamonds); PL with 3% P52–81(closed squares with white dot in center); PL with 7% p36–81 (open diamonds); PL with 3% p66–81 (closed squares); PL with 3% p1–15 (open squares) and PL control (closed triangles).

FIGS. 3A and 3B are two graphs that illustrate the results of another static compliance study of exemplary surfactants of the invention. The procedure was performed as described in FIG. 2 except that a different instillation procedure was used. The "x" and "y" axis and right and left graphs are as described in FIG. 2. The results for the following tested surfactants are illustrated: natural surfactant (open squares); phospholipid (PL) with 10% p51–81 (closed diamonds); PL with 10% p51–76 (closed squares); and PL (closed triangles).

In FIGS. 5A and 5B, the data for eight monkeys are shown; those which were later confirmed to have received $KL_4$-containing surfactant were identified as Monkey Nos. 6, 7, 8, and 10 (FIGS. 5A-3, 5A-4, 5B-1, and 5B-3), while those monkeys receiving another surfactant (i.e., one not containing a surfactant peptide of the present invention) were Monkey Nos. 3, 5, 9, and 11 (FIGS. 5A-1, 5A-2, 5B-2, and 5B-4). In all plots shown, a/A is plotted against hours after birth, with the time of administration of surfactant indicated. Data for the final $FiO_2$ (%), final $pCO_2$, final pH and lung expansion are also shown for each monkey.

DETAILED DESCRIPTION OF THE INVENTION

A. Definitions

Amino Acid

Figure 1:
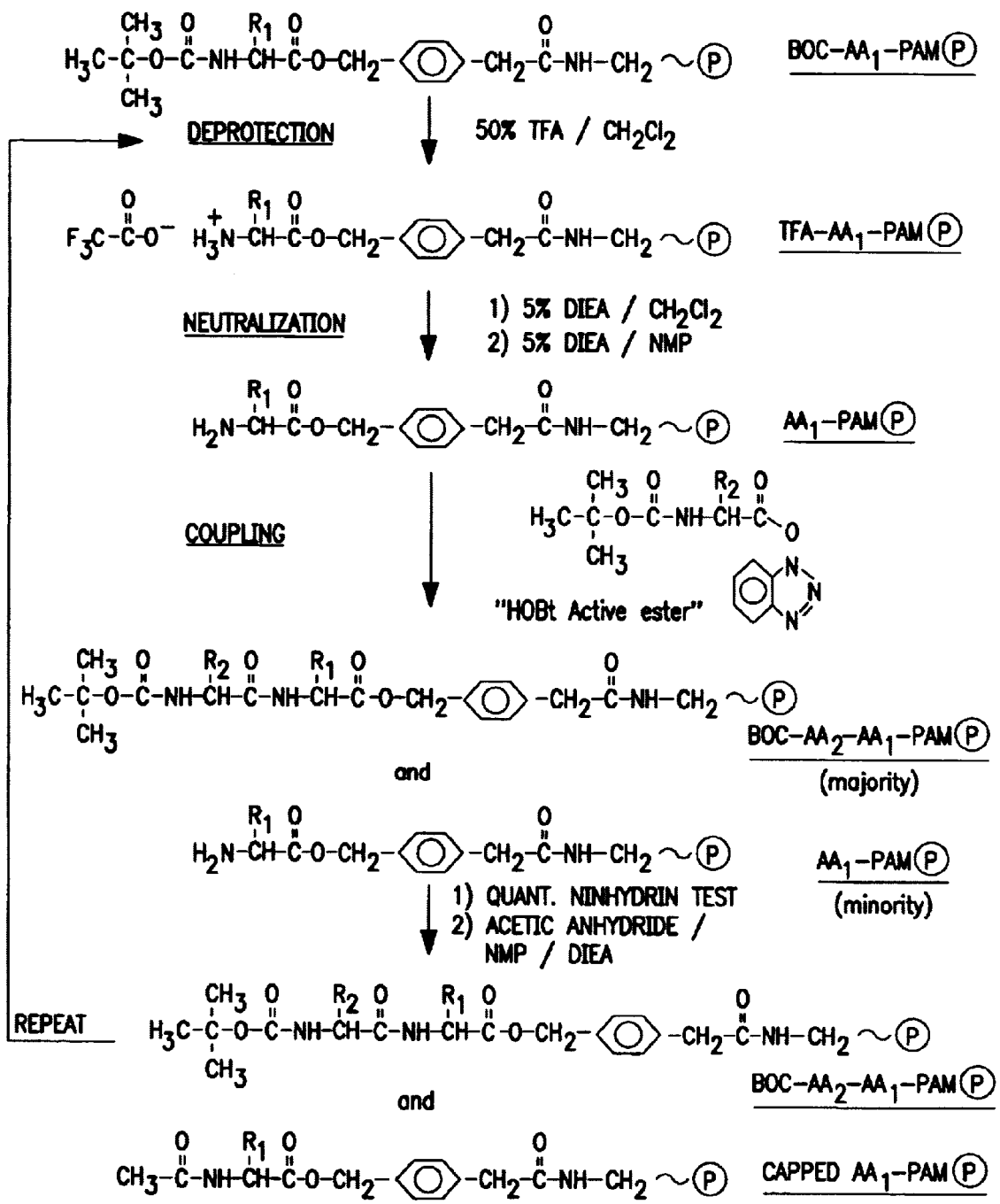
FIG. 1 illustrates the Merrifield method, which method may be used in the synthesis of a surfactant peptide of the present invention.

In various preferred embodiments, amino acid residues identified as useful are in the natural L-configuration. As disclosed hereinbelow, however, D-amino acids, substituted amino acids (e.g., amino acids with modified R groups) amino acid metabolites and catabolites, amino acids with "retro" backbones, and amino acid mimics or analogs are also contemplated for use in—and are thus encompassed by—the present invention.

In keeping with standard polypeptide nomenclature, *J. Biol. Chem.* 243: 3557–59, (1969), abbreviations for the more common amino acid residues are as shown in the following Table of Correspondence:

| Table of Correspondence | | |
|---|---|---|
| Symbol | | |
| 1-Letter | 3-Letter | Amino Acid |
| Y | Tyr | L-tyrosine |
| G | Gly | glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |
| X | Xaa | Unknown/other |

It should be noted that, unless otherwise indicated, the amino acid residue sequences represented herein by formulae have a left to right orientation in the conventional direction of amino-terminus to carboxy-terminus. In addition, the phrase "amino acid residue" is broadly defined to include the amino acids listed in the Table of Correspondence and modified and unusual amino acids, such as those listed in 37 C.F.R. §1.822(b)(4), and incorporated herein by reference. The phrase "amino acid residue" is also broadly defined to include D-amino acids, substituted amino acids (e.g., amino acids with modified R groups), modified amino acids (e.g., amino acid metabolites, catabolites, and amino acids with "designed" side chains), and amino acid mimics or analogs.

Furthermore, it should be noted that a dash at the beginning or end of an amino acid residue sequence generally indicates a bond to a radical such as H and OH (hydrogen and hydroxyl) at the amino- and carboxy-termini, respectively, or a further sequence of one or more amino acid residues. In addition, it should be noted that a virgule (/) at the right-hand end of a residue sequence indicates that the sequence is continued on the next line.

Pharmaceutically acceptable is a term that refers to molecular entities and compositions that do not produce an allergic or similar untoward reaction when administered to a human.

Polypeptide and peptide are terms used interchangeably herein to designate a linear series of no more than about 60 amino acid residues connected one to the other by peptide bonds between the alpha-amino and carboxy groups of adjacent residues.

Protein is a term used herein to designate a linear series of greater than about 60 amino acid residues connected one to the other as in a polypeptide.

Surfactant Activity

As used herein, the term refers to the ability of an organic molecule—e.g., a polypeptide—when combined with lipids, either alone or in combination with other organic molecules, to exhibit activity in the in vivo assay of Robertson, *Lung* 158: 57–68 (1980). In this assay, the sample to be assessed is administered through an endotracheal tube to fetal rabbits or lambs delivered prematurely by Caesarian section. (These "preemies" lack their own PS, and are supported on a ventilator.) Measurements of lung compliance, blood gases and ventilator pressure provide indices of activity. Preliminary assessment of surfactant activity may also be made by an in vitro assay, for example that of King, et al., *Am. J. Physiol.* 223: 715–726 (1972), or the assay illustrated hereinbelow, which utilizes a measurement of surface tension at an air-water interface when a protein or polypeptide is admixed with a phospholipid. In vitro assays of surfactant activity, which is assessed as the ability to lower the surface tension of a pulsating bubble, and in vivo assays utilizing fetal rabbits, as reported herein, are described in detail by Revak et al, *Am. Rev. Respir. Dis.* 134: 1258–1265 (1986).

B. Surfactant Compositions

Amino acid residue-containing molecules and other surfactant molecules of the present invention can be admixed with a pharmaceutically acceptable phospholipid to form a pulmonary surfactant (PS) useful in the treatment of respiratory distress syndrome. Phospholipids useful in forming alveolar surfactants by admixture with protein are well known in the art. See, Notter, et al, *Clin. Perinatology* 14: 433–79 (1987), for a review of the use of both native and synthetic phospholipids for surfactants.

The liposomal surfactant compositions that are prepared using a protein, a polypeptide, an amino acid residue-containing molecule, or another organic molecule of the present invention (collectively, "surfactant molecules") together with one or more phospholipids are eminently well suited for the treatment of Respiratory Distress Syndrome (RDS). Such surfactant compositions can contain about 50, usually about 80, to almost 100 weight percent lipid and about 50, usually about 20, to less than 1 weight percent surfactant molecule. The surfactant composition is prepared by admixing a solution of a surfactant molecule with a suspension of liposomes, or by admixing the surfactant molecule with a suspension of liposomes, or by admixing the surfactant molecule and lipids directly in the presence of organic solvent. Liposomal surfactant compositions of the present invention are generally sterile liposome suspensions containing a surfactant molecule of the present invention which has been combined with the lipids and a free fatty acid in an organic solvent system, dried, and then rehydrated.

In various preferred embodiments of the present invention, pulmonary surfactants effective in treating RDS comprising an effective amount of a surfactant molecule admixed with a pharmaceutically acceptable phospholipid are disclosed. In one preferred embodiment, the surfactant molecule is a polypeptide or protein; in others, the surfactant molecule is an organic molecule displaying surfactant activity which may comprise amino acid residues, modified amino acids, amino acid derivatives, amino acid analogs, and the like molecules, or other organic molecules mimicking that activity.

While methods for determining the optimal polypeptide-:phospholipid weight ratios for a given polypeptide-phospholipid combination are well known, we have determined that therapeutically effective ratios are in the range of about 1:5 to about 1:10,000, preferably about 1:100 to about 1:5,000, and more preferably about 1:500 to about 1:1000. In an even more preferred embodiment, the polypeptide-:phospholipid weight ratio is in the range of about 1:5 to about 1:2,000, preferably about 1:7 to about 1:1,000, and more preferably about 1:10 to about 1:100.

Thus, a pulmonary surfactant of this invention can contain about 50, usually about 80, to almost 100 weight percent lipid and about 50, usually about 20, to less than 1 weight percent polypeptide (or other surfactant molecule). Preferably a subject polypeptide is about 1 to about 10 weight percent of the surfactant for polypeptides corresponding to portions of the SP18 sequence and 1:100 for polypeptides corresponding to the entire SP18 monomer. (It should be remembered that SP18 may alternatively be called SP-B.) Similar ratios are appropriate for polypeptides and surfactant molecules which do not have amino acid residue sequences similar to that of SP18, but which demonstrate similar surfactant activity.

The lipid portion of a surfactant composition of the present invention is preferably about 50 to about 90, more preferably about 50 to about 75, weight percent dipalmitoylphosphatidylcholine (DPPC) with the remainder comprising unsaturated phosphatidyl choline, phosphatidyl glycerol (PG), triacylglycerols, palmitic acid, sphingomyelin or admixtures thereof. A pulmonary surfactant of the present invention is generally prepared by admixing a solution of a subject polypeptide with a suspension of liposomes or by admixing the subject polypeptide (or other organic surfactant molecule) and lipids directly in the presence of organic solvent. The solvent is then removed by dialysis or evaporation under nitrogen and/or exposure to vacuum.

A pulmonary surfactant composition is preferably formulated for endotracheal administration, e.g., typically as a liquid suspension, as a dry powder "dust", or as an aerosol. For instance, a surfactant (surfactant molecule-lipid micelle) is suspended in a liquid with a pharmaceutically acceptable excipient such as water, saline, dextrose, glycerol and the like. A surfactant-containing therapeutic composition can also contain small amounts of non-toxic auxiliary substances such as pH buffering agents, including sodium acetate, sodium phosphate, and the like. To prepare a surfactant in dust form, a surfactant is prepared as described herein, then lyophilized and recovered as a dry powder.

If it is to be used in aerosol administration, a subject surfactant is supplied in finely divided form along with an additional surfactant and propellent. Typical surfactants which may be administered are fatty acids and esters. However, it is preferred, in the present case, to utilize the other components of the surfactant complex, DPPC and PG. Useful propellants are typically gases at ambient conditions, and are condensed under pressure. Lower alkane and fluorinated alkane, such as Freon, may be used. The aerosol is packaged in a container equipped with a suitable valve so that the ingredients may be maintained under pressure until released.

A surfactant of the present invention is administered, as appropriate to the dosage form, by endotracheal tube, by aerosol administration, or by nebulization of the suspension or dust into the inspired gas. Amounts of PS between about 1.0 and about 400 mg/kg, preferably about 1.0 to 500 mg/kg, and more preferably about 50 mg to about 500 mg/kg, are administered in one dose. For use in newly born infants, one or two administrations are generally sufficient. For adults, sufficient reconstituted surfactant complex is preferably administered to produce a $PO_2$ within the normal range (see, e.g., Hallman, et al, *J. Clinical Investigation* 70: 673–682, 1982).

Polypeptides suitable for preparing liposomal surfactants in accordance with the present invention are further described in Section C immediately following.

Phospholipids useful in forming the present liposomal surfactant compositions by admixture with surfactant polypeptides are well known in the art. (See, e.g., Notter, et al, *Clin. Perinatology* 14: 433–79 (1987), for a review of the use of both native and synthetic phospholipids for surfactants.) Methods and materials useful in the preparation of preferred surfactant compositions as disclosed herein are also described in the Examples that follow.

To prepare a liposomal surfactant composition, the surfactant molecule or polypeptide molecule is dissolved in an organic solvent that maintains the molecule in its monomeric, substantially aggregate-free form. Preferred such solvents can be polar or non-polar and exhibit solubility parameter delta ($\delta$) values in the range of about 9 to about 15 $(cal.cm^3)^{1/2}$ or about 9 Hildebrand units (H) to about 15H.

Particularly preferred solvents are the hydrogen bonded solvents such as the $C_1$ to $C_4$ aliphatic alcohols, i.e., methanol ($\delta$=14.5H), ethanol ($\delta$=12.7H), n-propanol ($\delta$=11.9H), iso-propanol ($\delta$=11.5H), n-butanol ($\delta$=11.4H), iso-butanol ($\delta$=10.8H), etc. Among halogenated solvents particularly preferred are trifluoroethanol (TFE) and chloroform ($\delta$=9.3H). Mixtures or blends of aliphatic alcohols and halogenated solvents can be utilized as well.

In a preferred method for producing a liposomal surfactant composition, the polypeptide or other surfactant molecule is dissolved in the organic solvent together with the phospholipids, and the resulting solution is combined with an aqueous buffer solution. The resulting suspension is then dialyzed to remove the organic solvent. Alternatively, the organic solvent can be removed by evaporation and vacuum. The dried lipid/polypeptide mixture thus produced is rehydrated in an aqueous buffer system to produce the liposomes.

C. Proteins and Polypeptides

A protein or polypeptide of the present invention (subject protein or polypeptide) is characterized by its amino acid residue sequence and novel functional properties. A subject protein or polypeptide when admixed with a pharmaceutically acceptable phospholipid forms a pulmonary surfactant having a surfactant activity greater than the surfactant activity of the phospholipid alone. For example, a protein or polypeptide having a surfactant activity may exhibit a lower $\Delta P$, as shown in FIGS. 2 and 3 herein.

It is also to be understood that molecules comprising 60 or more amino acid residues—i.e. protein molecules—may be useful in surfactant compositions according to the present invention. While the present disclosure focuses primarily upon polypeptide molecules and molecules including amino acid residues, analogs, and/or other organic molecules, proteins having alternating hydrophobic and hydrophilic amino acid residue regions and proteins having surfactant ability as described herein are also contemplated by—and encompassed by—the present disclosures.

Molecules demonstrating surfactant activity which comprise 10 or fewer amino acid residues are also contemplated by the present invention. For example, a molecule comprising five amino acid residues linked to five amino acid derivatives or analogs may be useful as disclosed herein, particularly if it has alternating hydrophobic and hydrophilic amino acid residue regions and has surfactant ability, as defined herein. Thus, molecules comprising two to 100 amino acid residues having a configuration that maximizes their interaction with the alveoli are contemplated by the present invention. While larger molecules are somewhat more difficult to synthesize, it should be appreciated by those of skill in the relevant art that, as disclosed herein, even molecules containing 60 or more amino acid residues (or their analogs) may be excellent surfactants, provided they possess the within-disclosed characteristics.

Polypeptides suitable for preparing liposomal surfactants in accordance with the present invention can be synthesized from amino acids by techniques that are known to those skilled in the polypeptide art. An excellent summary of the many techniques available may be found in J. M. Steward and J. D. Young, "Solid Phase Peptide Synthesis", W. H. Freeman Co., San Francisco, 1969, and J. Meienhofer, "Hormonal Proteins and Peptides", Vol. 2, p. 46, Academic Press (New York), 1983 for solid phase peptide synthesis, and E. Schroder and K. Kubke, "The Peptides", Vol. 1, Academic Press (New York), 1965 for classical solution synthesis.

In general, these methods comprise the sequential addition of one or more amino acid residues or suitably protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group (e.g., lysine).

Using a solid phase synthesis as exemplary, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and any solid support) are removed sequentially or concurrently, to afford the final polypeptide. That polypeptide is then washed by dissolving in a lower aliphatic alcohol, and dried. The dried surfactant polypeptide can be further purified by known techniques, if desired. (Various methods of preparing polypeptides of the present invention are also described in the Examples below.)

Preferably, the surfactant polypeptides are polypeptides that include amino acid residue sequences having alternating charged and uncharged amino acid residue regions. Polypeptides including amino acid residue sequences having alternating hydrophobic and hydrophilic amino acid residue regions are also preferred according to the present invention. Particularly preferred surfactant polypeptides within these groupings are further characterized as having at least about 4, more preferably at least about 8, and even more preferably at least about 10 amino acid residues, and are generally not more than about 60 amino acid residues in length.

Preferably, surfactant polypeptides of the present invention are constituted by alternating groupings of charged amino acid residues and uncharged amino acid residues as represented by the formula $\{(Charged)_a(Uncharged)_b\}_c(Charged)_d$. Organic surfactant molecules not comprises solely of amino acid residues alone preferably have a similar structure constituted by alternating groupings of charged and uncharged (or hydrophilic/hydrophobic) constituent molecules.

In one preferred embodiment, surfactant polypeptides include a sequence having alternating groupings of amino acid residues as represented by the formula $(Z_a J_b)_c Z_d$, wherein Z is an amino acid residue independently selected from the group consisting of R, D, E, and K; J is an α-aminoaliphatic carboxylic acid.

In another embodiment, preferred polypeptides of the present invention have alternating groupings of amino acids residue regions as represented by the formula $(B_a U_b)_c B_d$, wherein B is an amino acid residue independently selected from the group consisting of H, 5-hydroxylysine, 4-hydroxyproline, and 3-hydroxyproline; and U is an amino acid residue independently selected from the group consisting of V, I, L, C, Y, and F. In one preferred variation, B is an amino acid derived from collagen and is preferably selected from the group consisting of 5-hydroxylysine, 4-hydroxyproline, and 3-hydroxyproline.

In still another preferred embodiment, surfactant polypeptides of the present invention include a sequence having alternating groupings of amino acid residues as represented by the formula $(B_a J_b)_c B_d$, wherein B is an amino acid residue independently selected from the group consisting of H, 5-hydroxylysine, 4-hydroxyproline, and 3-hydroxyproline; and J is an α-aminoaliphatic carboxylic acid.

Another preferred embodiment discloses surfactant polypeptides including a sequence having alternating groupings of amino acid residues as represented by the formula $(Z_a U_b)_c Z_d$, wherein Z is an amino acid residue independently selected from the group consisting of R, D, E, and K; and U is an amino acid residue independently selected from the group consisting of V, I, L, C, Y and F.

In the foregoing formulae, Z and U, Z and J, B and U, and B and J are amino acid residues that, at each occurrence, are independently selected. In addition, in each of the aforementioned formulae, a generally has an average value of about 1 to about 5; b generally has an average value of about 3 to about 20; c is 1 to 10; and d is 0 to 3.

In one variation of the foregoing embodiments, Z and B are charged amino acid residues. In other preferred embodiments, Z and B are hydrophilic or positively charged amino acid residues. In one variation, Z is preferably selected from the group consisting of R, D, E and K. In a related embodiment, Z is preferably selected from the group consisting of R and K. In yet another preferred embodiment, B is selected from the group consisting of H, 5-hydroxylysine, 4-hydroxyproline, and 3-hydroxyproline. In one preferred embodiment, B is H. In another preferred embodiment, B is a collagen constituent amino acid residue and is selected from the group consisting of 5-hydroxylysine, (δ-hydroxylysine), 4-hydroxyproline, and 3-hydroxyproline.

In various disclosed embodiments, U and J are, preferably, uncharged amino acid residues. In another preferred embodiment, U and J are hydrophobic amino acid residues. In one embodiment, U is preferably selected from the group consisting of V, I, L, C, Y, and F. In another preferred embodiment, U is selected from the group consisting of V, I, L, C, and F. In yet another preferred embodiment, U is selected from the group consisting of L and C. In various preferred embodiments, U is L.

Similarly, in various embodiments, B is an amino acid preferably selected from the group consisting of H, 5-hydroxylysine, 4-hydroxyproline, and 3-hydroxyproline. Alternatively, B may be selected from the group consisting of collagen-derived amino acids, which includes 5-hydroxylysine, 4-hydroxyproline, and 3-hydroxyproline.

In another embodiment of the present invention, charged and uncharged amino acids are selected from groups of modified amino acids. For example, in one preferred embodiment, a charged amino acid is selected from the group consisting of citrulline, homoarginine, or ornithine, to name a few examples. Similarly, in various preferred embodiments, the uncharged amino acid is selected from the group consisting of α-aminobutanoic acid, α-aminopentanoic acid, α-amino-2-methylpropanoic acid, and α-aminohexanoic acid.

In preferred embodiments of the present invention, items "a", "b", "c" and "d" are numbers which indicate the number of charged or uncharged residues (or hydrophilic or hydrophobic residues). In various embodiments, "a" has an average value of about 1 to about 5, preferably about 1 to about 3, more preferably about 1 to about 2, and even more preferably, 1.

In various embodiments, "b" has an average value of about 3 to about 20, preferably about 3 to about 12, more preferably about 3 to about 10, even more preferably in the range of about 4–8. In one preferred embodiment, "b" is about 4.

In various embodiments, "c" is 1 to 10, preferably 2 to 10, more preferably in the range of 3–8 or 4–8, and even more preferably 3 to 6. In one preferred embodiment, "c" is about 4.

In various embodiments, "d" is 0 to 3 or 1 to 3. In one preferred embodiment, "d" is 0 to 2 or 1 to 2; in another preferred embodiment, "d" is 1.

By stating that an amino acid residue—e.g., a residue represented by Z or U—is independently selected, it is meant that at each occurrence, a residue from the specified group is selected. That is, when "a" is 2, for example, each of the hydrophilic residues represented by Z will be independently selected and thus can include RR, RD, RE, RK, DR, DD, DE, DK, etc. By stating that "a" and "b" have average values, it is meant that although the number of residues within the repeating sequence (e.g., $Z_aU_b$) can vary somewhat within the peptide sequence, the average values of "a" and "b" would be about 1 to about 5 and about 3 to about 20, respectively.

Exemplary preferred polypeptides of the above formula are shown in Table 1 below:

TABLE 1

| Designation[1] | SEQ ID NO | Amino Acid Residue Sequence |
|---|---|---|
| KL4 | 1 | KLLLLKLLLLKLLLLKLLLLK |
| KL8 | 2 | KLLLLLLLLKLLLLLLLLKLL |
| KL7 | 3 | KKLLLLLLLLKKLLLLLLLKKL |
| DL4 | 4 | DLLLLDLLLLDLLLLDLLLLD |
| RL4 | 5 | RLLLLRLLLLRLLLLRLLLLR |
| RL8 | 6 | RLLLLLLLLRLLLLLLLLRLL |
| RL7 | 7 | RRLLLLLLLLRRLLLLLLLRRL |
| RCL1 | 8 | RLLLLCLLLRLLLLCLLLR |
| RCL2 | 9 | RLLLLCLLLRLLLLCLLLRLL |
| RCL3 | 10 | RLLLLCLLLRLLLLCLLLRLLLLCLLLR |
| HL4 | 13 | HLLLLHLLLLHLLLLHLLLLH |

[1]The designation is an abbreviation for the indicated amino acid residue sequence.

Also suitable are composite polypeptides of about 4 to 60 amino acid residues having a configuration that maximizes their interaction with the alveoli. A composite polypeptide consists essentially of an amino terminal sequence and a carboxy terminal sequence. The amino terminal sequence has an amino acid sequence of a hydrophobic region polypeptide or a hydrophobic peptide of this invention, preferably hydrophobic polypeptide, as defined in the above formula. The carboxy terminal sequence has the amino acid residue sequence of a subject carboxy terminal peptide.

Proteins and polypeptides derived from or similar to human SP18 (SP-B) surfactant protein are also useful as described herein. SP18 (SEQ ID NO 12; FIG. 4) has a large hydrophobic region (residues 1 to about 75), followed by a relatively short hydrophilic region at the carboxy terminus (residues 76 to 80, or 81). In referring to amino acid residue numbers of the SP18 sequence, those residues are as illustrated in FIG. 4. As disclosed herein, a variety of useful surfactant molecules adopt a configuration that mimics the alternating hydrophobic/hydrophilic pattern of the SP18 molecule.

In one embodiment, a surfactant molecule of the present invention comprises a polypeptide. In one variation, a surfactant polypeptide comprises about 4, more preferably about 10, amino acid residues. In various embodiments, a surfactant polypeptide preferably comprises 60 or fewer amino acid residues, more usually fewer than about 35, and even more preferably, fewer than about 25 amino acid residues. In various preferred embodiments, subject polypeptides correspond to the sequence of SP18 monomer. In other embodiments, subject polypeptides preferably have alternating charged and uncharged amino acid residue regions or have alternating hydrophobic and hydrophilic amino acid residue regions.

Thus, an exemplary amino acid sequence of a polypeptide of this invention may correspond to a single group of contiguous residues in the linear sequence of SP18. Polypeptides that correspond to more than one portion of the SP18 sequence are also contemplated. In various embodiments, at least one sequence that corresponds to about 10, preferably about 15, contiguous residues of the hydrophobic region of SP18 will be present in the peptide. A plurality of hydrophobic region amino acid sequences may be present, as well.

A subject polypeptide may include as its carboxy terminal sequence at least 5 contiguous residues in the linear sequence of SP18 including residue 80, or a sequence mimicking that carboxy terminal sequence in conformation, hydrophobicity, hydrophilicity, or charge. Thus, the polypeptides of this invention may include one or more groups of amino acid residues that correspond to portions of SP18 so that a sequence corresponding to a first group of contiguous residues of the SP18 monomer may be adjacent to a sequence corresponding to a second group of contiguous residues from the same or another portion of the SP18 monomer in the polypeptide. sequence. Peptides having two or more sequences that correspond to a single group of contiguous amino acid residues from the linear sequence of SP18 is also contemplated.

Some of the exemplary subject polypeptides corresponding in amino acid residue sequence to human SP18 monomer hydrophobic region are shown in Table 2.

TABLE 2

| Designation[1] | Amino Acid Residue Sequence |
|---|---|
| p1–15 | FPIPLPYCWLCRALI |
| p11–25 | CRALIKRIQAMIPKG |
| p21–35 | MIPKGALAVAVAQVC |
| p31–45 | VAQVCRVVPLVAGGI |
| p41–55 | VAGGICQCLAERYSV |
| p46–76 | CQCLAERYSVILLDTLLGRMLPQLVCRLVLR |
| p51–65 | ERYSVILLDTLLGRM |
| p51–72 | ERYSVILLDTLLGRMLPQLVCR |
| p51–76 | ERYSVILLDTLLGRMLPQLVCRLVLR |
| p54–72 | SVILLDTLLGRMLPQLVCR |
| p54–76 | SVILLDTLLGRMLPQLVCRLVLR |
| p61–75 | LLGRMLPQLVCRLVL |

[1]The designation of each peptide indicates that portion of the amino acid residue sequence of human SP18 monomer, as shown in FIG. 4, to which the peptide sequence corresponds -- i.e., it indicates the location of the peptide sequence in the protein sequence.

In various other embodiments, a subject polypeptide is further characterized as having a carboxy-terminal amino acid residue sequence represented by the formula:

-RLVLRCSMDD$_Z$, wherein Z is an integer having a value of 0 or 1 such that when Z is 0 the D residue to which it is a subscript is absent and when Z is 1 the D residue to which it is a subscript is present. Exemplary "carboxy-terminal polypeptides" are shown in Table 3.

TABLE 3

| Designation[1] | Amino Acid Residue Sequence |
|---|---|
| p71–81 | C RLVLRCSMDD |
| p66–81 | LPQLVCRLVLRCSMDD |
| p59–81 | DTLLGRMLPQLVCRLVLRCSMDD |
| p52–81 | RYSVILLDTLLGRMLPQLVCRLVLRCSMDD |
| P51–81 | ERYSVILLDTLLGRMLPQLVCRLVLRCSMDD |
| P51–80 | ERYSVILLDTLLGRMLPQLVCRLVLRCSMD |
| p36–81 | RVVPLVAGGICQCLAERYSVILLDTLLGRMLPQLVCRLVLRCSMDD |
| p32–81 | AQVCRVVPLVAGGICQCLAERYSVILLDTLLGRMLPQLVCRLVLRCSMDD |

[1]The designation is the same as in Table 2.

In various preferred embodiments, a subject polypeptide has an amino acid residue sequence that corresponds to a portion of the sequence shown in FIG. 4. However, it should be understood that a polypeptide of the present invention need not be identical to the amino acid residue sequence of a native SP18 monomer. Therefore, a polypeptide of the present invention can be subject to various changes, such as insertions, deletions and substitutions, either conservative or non-conservative, where such changes provide for certain advantages in their use.

Conservative substitutions are those in which one amino acid residue is replaced by another, biologically similar residue. Examples of conservative substitutions include the substitution of one hydrophobic residue such as isoleucine, valine, leucine or methionine for another, or the substitution of one polar residue for another such as between arginine and lysine, between glutamic and aspartic acids or between glutamine and asparagine and the like. The term "conservative substitution" also includes the use of a substituted amino acid in place of an unsubstituted parent amino acid provided that such a polypeptide also displays the requisite binding activity. Thus, in one preferred embodiment, a serine (S) residue is substituted for a cysteine (C) residue, usually at least one of residue positions 71 and 77. Preferably the serine analog has a sequence corresponding to the sequence of residues 51–76 of the SP18 monomer with the substitution at residue 71 or to the sequence of residues 51–81 with serine substitutions at 71 and 77.

When a polypeptide of the present invention has a sequence that is not identical to the sequence of a native SP18 monomer because one or more conservative or non-conservative substitutions have been made, usually no more than about 20 number percent and more usually no more than 10 number percent of the amino acid residues are substituted, except where additional residues have been added at either terminus as for the purpose of providing a "linker" by which the polypeptides of this invention can be conveniently affixed to a label or solid matrix, or carrier. Labels, solid matrices and carriers that can be used with the polypeptides of this invention are described hereinbelow.

Amino acid residue linkers are usually at least one residue and can be 40 or more residues, more often 1 to 10 residues that do not correspond in amino acid residue sequence to a native SP18 monomer. Typical amino acid residues used for linking are tyrosine, cysteine, lysine, glutamic and aspartic acid, or the like. In addition, a polypeptide sequence of this invention can differ from the natural sequence by the sequence being modified by terminal-NH$_2$ acylation, e.g., acetylation, or thioglycolic acid amidation, terminal-carboxlyamidation, e.g., ammonia, methylamine, etc.

In another embodiment, a polypeptide of this invention has amino acid residue sequence that has a composite hydrophobicity of less than zero, preferably less than or equal to −1, more preferably less than or equal to −2. Determination of the composite hydrophobicity value for a peptide is described in detail in Example 3. These hydrophobic polypeptides perform the function of the hydrophobic region of SP18. Thus, in one preferred embodiment, the amino acid sequence mimics the pattern of charged and uncharged—or hydrophobic and hydrophilic—residues of SP18.

It should be understood, however, that polypeptides and other surfactant molecules of the present invention are not limited to molecules having sequences like that of native SP18. On the contrary, some of the most preferred surfactant molecules of the present invention have little resemblance to SP18 with respect to a specific amino acid residue sequence, except that they have similar surfactant activity and alternating charged/uncharged (or hydrophobic/hydrophilic) residue sequences.

D. Amino Acids, Natural Metabolites, Derivatives, Designed Analogs, and Other Organic Molecules Surfactant molecules of the present invention also include organic molecules having surfactant activity, as defined above and as further described herein. While polypeptides and proteins are often described as exemplary, it should be understood that surfactant molecules of the present invention are not limited to those having either conventional amino acid side chains or a polyamide backbone structure.

As noted previously, the present invention contemplates a variety of surfactant molecules, including proteins, polypeptides, and molecules including amino acid residues, as well as a variety of surfactant compositions. While one tends to think of the "common" natural amino acids (i.e., those listed in the "Table of Correspondence" in Section A above) as being preferred for use in biological compositions, it is also true that a wide variety of other molecules, including uncommon but naturally occurring amino acids, metabolites and catabolites of natural amino acids, substituted amino acids, and amino acid analogs, as well as amino acids in the "D" configuration, are useful in molecules and compositions of the present invention. In addition, "designed" amino acid derivatives, analogs and mimics are also useful in various compounds, compositions and methods of the present invention, as well as polymers including backbone structures composed of non-amide linkages.

For example, in addition to the L-amino acids listed in the "Table of Correspondence" in Section A above, amino acid metabolites such as homoarginine, citrulline, ornithine, and α-aminobutanoic acid are also useful in molecules and compositions of the present invention. Thus, in the various formulas described above, "Charged", Z, or B may comprise homoarginine, citrulline, or ornithine, as well as a variety of other molecules as identified herein. Similarly, J may comprise α-aminobutanoic acid (also known as α-aminobutyric acid), α-aminopentanoic acid, α-aminohexanoic acid, and a variety of other molecules identified herein.

Further, substituted amino acids which are not generally derived from proteins, but which are known in nature, are useful as disclosed herein, include the following examples: L-canavanine; 1-methyl-L-histidine; 3-methyl-L-histidine; 2-methyl L-histidine; α,ε-diaminopimelic acid (L form, meso form, or both); sarcosine; L-ornithine betaine; betaine of histidine (herzynine); L-citrulline; L-phosphoarginine; D-octopine; O-carbamyl-D-serine; γ-aminobutanoic acid; and βB-lysine. D-amino acids and D-amino acid analogs, including the following, are also useful in proteins, peptides and compositions of the present invention: D-alanine, D-serine, D-valine, D-leucine, D-isoleucine, D-alloisoleucine, D-phenylalanine, D-glutamic acid, D-proline, and D-allohydroxyproline, to name some examples. The foregoing may also be used in surfactant molecules according to the present invention; particularly preferred for use accordingly are those corresponding to the formula $\{(Charged)_a(Uncharged)_b\}_c(Charged)_d$.

The present invention also discloses that an extensive variety of amino acids, including metabolites and catabolites thereof, may be incorporated into molecules which display a surfactant activity. For example, molecules such as ornithine, homoarginine, citrulline, and α-aminobutanoic acid are useful components of molecules displaying surfactant activity as described herein. Surfactant molecules according to the present invention may also comprise longer straight-chain molecules; α-aminopentanoic acid and α-aminohexanoic acid are two additional examples of such useful molecules.

It should also be appreciated that the present invention encompasses a wide variety of modified amino acids, including analogs, metabolites, catabolites, and derivatives, irrespective of the time or location at which modification occurs. In essence, one may place modified amino acids into three categories: (1) catabolites and metabolites of amino acids; (2) modified amino acids generated via posttranslational modification (e.g., modification of side chains); and (3) modifications made to amino acids via non-metabolic or non-catabolic processes (e.g., the synthesis of modified amino acids or derivatives in the laboratory).

"Designer" or "Designed" Molecules

The present invention also contemplates that one may readily design side chains of the amino acids of residue units that include longer or shortened side chains by adding or subtracting methylene groups in either linear, branched chain, or hydrocarbon or heterocyclic ring arrangements. The linear and branched chain structures may also contain non-carbon atoms such as S, O, or N. Fatty acids may also be useful constituents of surfactant molecules herein. The designed side chains may terminate with (R') or without (R) charged or polar group appendages. Examples of side chains that may be included in surfactant molecules of the present invention include those presented hereinbelow.

For example, a component of a designer molecule may take the configuration:

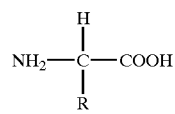

or it may have the following configuration:

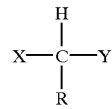

where the symbols "X" and "Y" represent linking groups other than amino ($NH_2-$) or carboxyl ($-COOH$) groups.

Exemplary R and R' groups include the following:

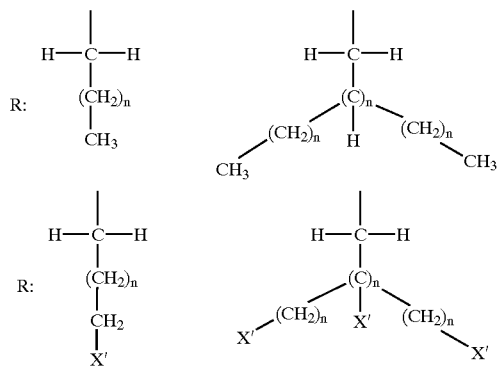

In the foregoing examples, X' may represent a charged or polar group, such as $-COOH$, $-OH$, $-NH_2$, $-NH-(NH=)C-NH_2$, $-SO_4H$, $-PO_4H$, or SH, to name a few examples. (Note: the guanidino group, $-NH-(NH=)C-NH_2$, may also be illustrated as follows:

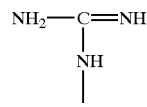

In addition, analogs, including molecules resulting from the use of different linkers, are also useful as disclosed herein. Molecules with side chains linked together via linkages other than the amide linkage—e.g., molecules containing amino acid side chains or other side chains (R—or R'—) wherein the components are linked via carboxy- or phospho-esters, ethylene, methylene, ketone or ether linkages, to name a few examples—are also useful as disclosed herein. In essence, any amino acid side chain, R or R' group-containing molecule may be useful as disclosed herein, as long as the molecule includes alternating hydrophilic and hydrophobic residues (i.e., component molecules) and displays surfactant activity as described herein.

Some examples of useful linkers/linkages include the following:

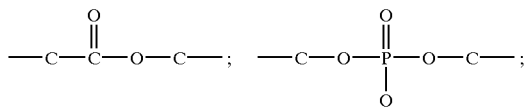

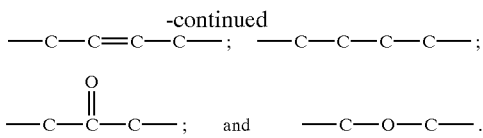

The present invention also contemplates molecules comprising peptide dimers joined by an appropriate linker—e.g., peptide dimers linked by cystine molecules. (As those of skill in the art are aware, two cysteine molecules may be linked together by a disulfide bridge formed by oxidation of their thiol groups.) Such linkers or bridges may thus cross-link different polypeptide chains, dimers, trimers, and the like. Other useful linkers which may be used to connect peptide dimers and/or other peptide multimers include those listed above—e.g., carboxy- or phospho-ester, ethylene, methylene, ketone or ether linkages, to name a few examples.

While it is appreciated that many useful polypeptides disclosed herein—e.g., the KL4 polypeptide (SEQ ID NO 1)—comprise naturally-occurring amino acids in the "L" form which are joined via peptide linkages, it should also be understood that molecules including amino acid side chain analogs, non-amide linkages (e.g., differing backbones) may also display a significant surfactant activity and may possess other advantages, as well. For example, if it is desirable to construct a molecule (e.g., for use in a surfactant composition) that is not readily degraded, one may wish to synthesize a polypeptide molecule comprising a series of D-amino acids. Molecules comprising a series of amino acids linked via a "retro" backbone—i.e., a molecule that has internal amide bonds constructed in the reverse direction of carboxyl terminus to amino terminus—are also more difficult to degrade and may thus be useful in various applications, as described herein. For example, the following illustrates an exemplary molecule with a "retro" bond in the backbone:

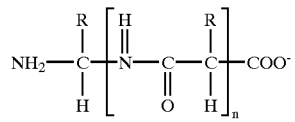

In another variation, one may wish to construct a molecule that adopts a more "rigid" conformation; one means of accomplishing this would be to add methyl or other groups to the α carbon atom of the amino acids. The following diagram represents an example (with the methyl group on the α carbon atom highlighted in bold):

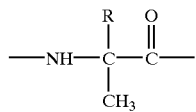

As noted above, other groups besides a $CH_3$ group may be added to the α carbon atom—that is, surfactant molecules of the present invention are not limited to those incorporating a $CH_3$ at the α carbon alone. For example, any of the side chains and molecules described and exemplified above—e.g., the exemplary R and R' groups illustrated above—may be substituted for the indicated $CH_3$ group at the a carbon component.

Analogs, Derivatives, and Other Modifications

As used herein, the terms "analogs" and "derivatives" of polypeptides and amino acid residues are intended to encompass metabolites and catabolites of amino acids, as well as molecules which include linkages, backbones, side-chains or side-groups which differ from those ordinarily found in what are termed "naturally-occurring" L-form amino acids. (The terms "analog" and "derivative" may also conveniently be used interchangeably herein.) Thus, D-amino acids, molecules which mimic amino acids and amino acids with "designed" side chains (i.e., that can substitute for one or more amino acids in a molecule having surfactant activity) are also encompassed by the terms "analogs" and "derivatives" herein.

A wide assortment of useful surfactant molecules, including amino acids having one or more extended or substituted R or R' groups, is also contemplated by the present invention. Again, one of skill in the art should appreciate from the within disclosures that one may make a variety of modifications to individual amino acids, to the linkages, and/or to the chain itself—which modifications will produce molecules falling within the scope of the present invention—as long as the resulting molecule possesses surfactant activity as described herein.

The following examples are intended to illustrate, but not limit, the present invention.

EXAMPLES

Example 1

Preparation of Surfactant Compositions

Materials 1,2-dipalmitoyl phosphatidylcholine (DPPC) and 1-palmitoyl, 2-oleoyl phosphatidylglycerol (POPG), and palmitic acid (PA) were obtained from Avanti Polar Lipids Inc. (Birmingham, Ala.). L-α-Dipalmitoyl-[dipalmitoyl-1-$^{14}$C]-phosphatidylcholine ($^{14}$C-DDC) was obtained from New England Nuclear (Boston, Mass.). $KL_4$ peptide with the amino acid sequence KLLLLKLLLLKLLLLKLLLLK was synthesized as described herein or obtained from the R. W. Johnson Pharmaceutical Research Institute (La Jolla, Calif.). All salts, buffers and organic solvents used were of the highest grade available.

Procedures

Synthesis of a peptide of the present invention—e.g., $KL_4$—may be carried out according to a variety of known methods of synthesis. The following procedure is described as exemplary. $KL_4$ peptide (9 mg), DPPC (225 mg), POPG (75 mg) and PA (45 mg) were dissolved in 2.5 milliliters (ml) of 95% ethanol at 45° C. This solution was then added to 7.5 ml of distilled $H_2O$ at 45° C. with rapid vortexing and 2 ml of 500 mM NaCl, 250 mM. Tris-acetate pH 7.2 was subsequently added. The resulting milky suspension was stirred at 37° C. for 15 minutes and the ethanol present was then removed by dialysis (Spectrapor 2; 13,000 mol. wt. cutoff) against 100 volumes of 130 mM NaCl, 20 mM Tris-acetate pH 7.2 buffer at 37° C. Dialysis was continued for 48 hours with two changes of the dialysis solution.

Alternatively, the following procedure is also useful in synthesizing batches of peptide—e.g., $KL_4$ peptide—used as described herein. Chemicals and reagents used in the synthesis of surfactant peptides include the following:

t-Boc-L-lysine(Cl-Z) PAM-resin (t-Boc-L-Lys(Cl-Z); Applied Biosystems (Foster City, Calif.));
a-Boc-ε-(2-Chloro-CBZ)-L-Lysine (Bachem (San Diego, Calif.));
N-Boc-L-Leucine-$H_2O$ (N-Boc-L-Leu; Bachem);
Dichloromethane (DCM; EM Science (Gibbstown, N.J.) or Fisher (Pittsburgh, Pa.);

Trifluoroacetic acid (TFA; Halocarbon);
Diisopropylethylamine (DIEA; Aldrich (Aldrich, Mich.));
N,N-Dimethylformamide (DMF; EM Science (Gibbstown, N.J.));
Dimethylsulfoxide (DMSO; Aldrich);
N-Methylpyrrolidone (NMP; Burdick & Jackson (Muskegon, Mich.));
1-Hydroxybenzotriazole hydrate (HOBt; Aldrich);
1,3-Dicyclohexylcarbodiimide (DCC; Aldrich);
Acetic anhydride ($Ac_2O$; Mallinckrodt (St. Louis, Mo.)); and
Hydrogen fluoride (HF; Air Products (Allentown, Pa.)).

One means of synthesizing $KL_4$ peptide is performed on a Coupler 296 Peptide Synthesizer (Vega Biotechnologies, Tucson, Ariz.) using the Merrifield method (see FIG. 1). A "typical" synthesis is described as follows. Chain elongation was carried out on 100 g of lysine PAM-resin by the procedure described in Table 4 below. All steps except steps 7, 10 and 11 were done automatically.

TABLE 4

Program for a Cycle Using the HOBt Active Ester Procedure

| Step | Reagent | Time | Volume |
|---|---|---|---|
| 1 | 50% TFA/$CH_2Cl_2$ | 1 × 2 min | 1.8 liters |
| 2 | 50% TFA/$CH_2Cl_2$ | 1 × 20 min | 1.5 liters |
| 3 | $CH_2Cl_2$ | 5 × 20 sec | 1.7 liters |
| 4 | 5% DIEA/$CH_2Cl_2$ | 1 × 2 min | 1.7 liters |
| 5 | 5% DIEA/NMP | 1 × 3 min | 1.7 liters |
| 6 | DMF | 5 × 30 sec | 1.7 liters |
| 7 | BOC AA-HOBt active ester | 1 × 39 min | 1.0 liters |
| 8 | DIEA/DMSO (195 ml/285 ml) | 1 × 21 min | 0.5 liters |
| 9 | DMF | 3 × 30 sec | 1.7 liters |
| 10 | 10% $Ac_2O$/ 5% DIEA/NMP | 1 × 8 min | 2.0 liters |
| 11 | $CH_2Cl_2$ | 3 × 30 sec | 1.7 liters |

While the peptide-resin was being deprotected, the appropriate amino acid derivative was being made. The appropriate amino acid was dissolved in one (1) liter of NMP. After a clear solution was obtained, HOBt was added to the solution. When the HOBt was dissolved, DCC was added to the solution. This solution was left stirring for one (1) hour at room temperature. During this one hour of stirring, a by-product formed, dicyclohexylurea (a white precipitate). This by-product was filtered off through a buchner funnel using Whatman's #1 filter paper. The filtrate was then added manually to the contents of the Vega 296 reaction vessel at step No. 7.

The synthesizer was then programmed to stop after the completion of step No. 9. Aliquots of the peptide resin were subjected to the quantitative ninhydrin test of Sarin et al. (Applied; Biosystems 431A user manual, Appendix A). The coupling efficiencies were good throughout the entire synthesis. The unreacted peptide resin was acetylated after leucine 12 (cycle 9) and after leucine 5 (cycle 16). After each acetylation, the peptide resin was washed with dichloromethane (see Table 4, step 11).

At the end of the synthesis, the completed peptide resin was deprotected (removal of the Boc group) by completing steps 1–3 of the program (see Table 4). The deprotected peptide resin was then washed with ample volumes of absolute ethanol and dried in vacuo over $P_2O_5$. The weight of the dried, deprotected peptide resin was 256.48 grams. Since the batch was started with 100 g of t-Boc-Lysine (Cl-Z) $OCH_2$ PAM resin at a substitution of 0.64 mmoles/gram, the load corresponded to 64 mmoles. Subtracting out the initial 100 grams of resin, the weight gain was 156.48 grams. The molecular weight of the nascent protected peptide (excluding the C-terminal lysine anchored onto the resin) was 3011.604 g/mole.

HF Cleavage

The 256.48 gram lot of peptide resin was treated with hydrogen fluoride (HF) in three large aliquots. A Type V HF-Reaction Apparatus from Peninsula Laboratories (Belmont, Calif.) was used for the cleavage of the peptide resin using liquid hydrogen fluoride. the anisole was distilled before use. HF was used without any treatment. Dry ice, isopropanol and liquid nitrogen are required for cooling purposes.

For the first HF, approximately 88 g of the $KL_4$ peptide resin was placed into the one-liter reaction vessel with a magnetic stir bar. Twenty-five ml of distilled anisole was added to the peptide resin. After the entire system was assembled and leak-tested, HF was condensed into the reaction vessel until the overall level reached about 300 ml. Cleavage of the peptide from the resin was allowed to proceed for one hour at −4° C. Partial removal of HF was done by water aspirator for 1–2 hours. After the 1–2 hours, the rest of the HF was removed by high vacuum (mechanical vacuum pump) for 1–2 hours. The temperature of the reaction vessel remained at −4° C. throughout the HF removal process.

The HF apparatus was then equilibrated to atmospheric pressure and an oily sludge was found at the bottom of the reaction vessel. Cold anhydrous ether (700 ml, prechilled to −20° C.) was added to the contents of the reaction vessel. The resin clumps were triturated with ether using a glass rod. The ether was decanted after the resin settled. The resin was then washed with 500 ml of room temperature anhydrous ether and allowed to stir for about 5 min. The ether was decanted after the resin settled. The resin was washed until it became free-flowing (4–5 total washes). The resin was left in the fume hood to dry overnight.

The resulting dried HF-treated resin was then weighed and stored in the freezer. 1.021 grams of the dried HF-treated resin was removed and extracted with 50 ml of 50% acetic acid/water and allowed to stir for 30 min. The resin was filtered through a coarse sintered glass funnel, and the filtrate was collected in a lyophilizing jar. The filtrate was diluted with approximately 200 ml of water, shell frozen, and placed on the lyophilizer. The one (1) gram of extracted HF-treated resin yielded 569 mg of crude peptide. The following table summarizes the large scale HF treatments of the remaining $KL_4$ peptide resin.

| HF# | Wt. of Resin | Amt. of Anisole | Total Volume (HF + Anisole + Resin) |
|---|---|---|---|
| 1 | 88.07 g | 25 ml | 300 ml |
| 2 | 85.99 g | 25 ml | 300 ml |
| 3 | 79.35 g | 25 ml | 300 ml |

All of the HF-treated Resins were Stored in the Freezer.

Purification

The peptide was purified using a Dorr-Oliver Model B preparative HPLC (Dorr-Oliver, Inc., Milford, Conn.). This unit was connected to a Linear Model 204 spectrophotometer and Kipp and Zonen dual channel recorder. This preparative HPLC was interfaced with a Waters KIL250 Column Module (Waters Associates, Milford, Mass.) containing a radially compressed 10×60 cm cartridge filled with Vydac $C_4$ support, 15–20 microns, and 300 A pore size (Vydac, Hesperia, Calif.). Solvent "A" consisted of 0.1% HOAc in water, and solvent "B" consisted of 0.1% HOAc in acetonitrile. The flow rate was set at 400 ml/min, the cartridge was compressed to 150–200 psi, and the preparative HPLC system back pressure was at 550–600 psi.

For the first Dorr-Oliver run, 20 g of the HF treated resin from HF#1 was extracted in 500 ml of glacial acetic acid for five minutes. Water (500 ml) was added to the resin/acetic acid mixture. This 50% acetic acid/water solution was stirred for an additional 25 minutes. The resin was filtered off with a coarse sintered glass funnel. The peptide-containing filtrate was saved and loaded onto the Dorr-Oliver. The HPLC gradient used was 1–40% "B" in 45 minutes, then held isocratically for seven minutes. At this point, the percent "B" was increased 1% per minute to a final percentage of 44% (not shown).

Fractions were collected manually and were analyzed by HPLC. All fractions that met a purity of $\geq 95\%$ were pooled together and stored in a large glass container. This material was subsequently referred to as "BPS #1." All fractions that had the desired component, but did not meet the 95% or better purity, were collected and later recycled. At least 10 additional preparative HPLC runs were performed on the Dorr-Oliver unit (data not shown).

Reverse Osmosis, Lyophilization

The total volume of BPS #1 was approximately 60 liters. Reverse osmosis was used to concentrate the peptide solution to a final volume of two liters. A Millipore Model 6015 Reverse Osmosis Unit with an R74A membrane to retain the peptide was used. The resulting two liters of BPS #1 were filtered through a buchner funnel using two pieces of Whatman #1 filter paper, divided into approximately 11 lyophilizing jars and diluted with equal volumes of water. The lyophilizing jars were shell-frozen and lyophilized. The total weight of dry $KL_4$ peptide at the end of the procedure was 40.25 g.

Re-lyophilization

It has been found that different lyophilizing conditions (e.g. peptide concentration, composition of solvents to be lyophilized, length of the lyophilization step, shelf temperature, etc.) can result in dried preparations having differing solubility characteristics. It is desirable that the dry $KL_4$ peptide be soluble in a chloroform:methanol (1:1) solution at 1mg/ml and $\geq 90\%$ soluble at 10 mg/ml. If these criteria are not met at the end of the lyophilization step noted above, the peptide can be re-lyophilized. A typical re-lyophilization is described as follows.

Approximately 5 g of peptide is slowly added to two liters of acetonitrile stirring in a glass flask. After approximately one minute, three liters of Milli-Q water is added, followed by 50 ml of acetic acid (final concentration of acetic acid= 1%). This is stirred for three days at 37° C., filtered through Whatman #1 filter paper in a buchner funnel, and placed into a lyophilization jar. It is then shell frozen using dry ice and isopropyl alcohol and placed on the lyophilizer. Lyophilization time may vary from three to seven days. The final dry product is then weighed, packaged, and aliquots taken for solubility and chemical analyses.

Example 2

Pharmaceutical Formulations

In various aspects of the present invention, individuals with IRDS or ARDS may receive therapeutic doses of surfactant-containing compositions as disclosed herein. Preferably, surfactants of the present invention are administered intratracheally, although other routes of administration may be contemplated as well. While the formulation of some exemplary surfactant compositions—e.g., liposomal surfactant compositions including $KL_4$ peptide—are described hereinbelow, it is expressly to be understood that formulations including molecules and compounds of the present invention in addition to—or substituting for—$KL_4$ peptide are contemplated by the present invention.

For example, in one embodiment of the present invention, a surfactant composition of the present invention comprises, in each ml of composition, 0.80 mg $KL_4$ peptide, 19.95 mg DPPC, 6.65 mg POPG, and 3.99 mg PA. In various embodiments, the surfactant is prepared aseptically and is supplied in vials containing a sufficient volume to deliver either 2 ml or 5 ml of the suspension. Thus, in one exemplary formulation, a preparation having a phospholipid concentration of about 26.6 mg/ml administered at a dosage volume of about 5.0 ml/kg would result in a dose of about 133 mg/kg. Similarly, an exemplary preparation having a phospholipid concentration of about 35 mg/ml administered at a dosage volume of about 5.7 ml/kg would result in a dose of about 200 mg/kg.

One preferred final surfactant composition comprises a sterile liposome suspension containing surfactant polypeptide (or other surfactant molecules according to the present invention). By way of illustration, a drug product/surfactant composition containing $KL_4$ peptide is described as exemplary.

Peptide is preferably combined with lipids and free fatty acid in an organic solvent system which is then removed by evaporation and vacuum. The dried lipid/peptide mixture is rehydrated in an aqueous buffer system, allowing liposomes to form. While in the organic solvents, the drug components are sterile-filtered and all subsequent processing is performed aseptically.

One exemplary composition comprises surfactant peptide and a lipid component. In one embodiment, the lipid component comprises DPPC and/or POPG. In other preferred compositions, the composition also comprises palmitic acid (PA).

For example, a surfactant composition including $KL_4$ peptide may be prepared from an admixture of DPPC and POPG in a 3:1 ratio by weight with palmitic acid (PA), 15% by weight compared with the phospholipids, in an organic solvent. $KL_4$ peptide is prepared in the surfactant dispersion as 3% by weight of the phospholipid concentration. Organic solvents were removed from the lipid/peptide mixture by evaporation under nitrogen and vacuum. A Tris buffer solution was added to form liposomes of the peptide-containing surfactant.

A Tham buffer system may also be included in a surfactant composition of the present invention. (Tham is a buffering agent also known as Tris, tromethamine, and tris (hydroxymethyl)aminomethane.) In various preferred embodiments, the compositions have a pH range of about 6.5–8.0.

A Tham buffer system may be prepared essentially as follows. 0.37 ml of Tham solution (tromethamine injection, NDC 0074-1593-04, Abbott Laboratories, North Chicago, Ill.), pH adjusted with acetic acid (AR Select, ACS, Mallinckrodt, Paris, Ky.) to a pH of 7.2±0.5, is admixed with 0.33 ml saline (0.9% sodium chloride injection, USP, Abbott Laboratories) and 0.30 ml water (sterile water for injection, USP, Abbott Laboratories) and is sterile-filtered.

Thus, in one preferred embodiment, a surfactant composition of the present invention comprises about 0.80 mg peptide, 19.95 mg DPPC, 6,65 mg POPG, 3.99 mg PA, and 1 ml Tham buffer system, per ml of the composition. In another preferred embodiment, a surfactant composition of the present invention includes the following components per ml of Tham buffer of physiologic pH and osmolality: Peptide, 1.05 mg; DPPC, 26.25 mg; POPG, 8.75 mg; and PA, 5.25 mg. Surfactant compositions are preferably prepared aseptically and are supplied as sterile, non-pyrogenic solutions in vials containing sufficient volume to deliver either 2 ml or 6 ml of the suspension.

Surfactant compositions may be formulated to contain 40 mg/mL total phospholipid, with a composition based on the following formula: $PL_T$=total phospholipid=DPPC+POPG 3 DPPC:1 POPG 1 $PL_T$:0.15 PA:0.03 peptide.

Using the foregoing formula, the preferred composition per mL of finished product is essentially as follows:

| Component | Amount per mL |
|---|---|
| DPPC | 30.0 mg |
| POPG | 10.0 mg |
| PA | 6.0 mg |
| Peptide | 1.2 mg |

In addition, with regard to the buffer system/suspension, the composition may further comprise, per mL of finished product:

| Component | Amount per mL |
|---|---|
| Tromethamine, USP | 2.42 mg |
| Glacial acetic acid or NaOH, NF | quantity sufficient to adjust tromethamine buffer to pH 7.7 |
| NaCl, USP | 7.6 mg |
| Water for injection, USP | quantity sufficient to 1.0 mL |

In various preferred embodiments, an administered amount of surfactant—i.e., a surfactant of the present invention—provides a dose of about 50 mg/kg, 100 mg/kg, 133 mg/kg, or 200 mg/kg, measured in terms of total phospholipid content. It must be appreciated that the treatment regimen may vary from individual to individual, depending on the severity of the RDS, the symptoms present, and other relevant variables; thus, single or multiple doses may be administered to an individual.

Example 3

In Vitro Assessment of Polypeptide Surfactant Activity

Measurement of Surfactant Activity

Measurements of surface pressure across an air-liquid interface (expressed in negative cm of $H_2O$ pressure) at minimal (γmin) bubble radius were determined at various times using the pulsating bubble technique described by Enhorning, *J. Appl. Physiol.* 43: 198–203 (1977).

Briefly, the Enhorning Surfactometer (Surfactometer International, Toronto, Ontario) measures the pressure gradient (ΔP) across a liquid-air interface of a bubble that pulsates at a rate of 20 cycles/min between a maximal (0.55 mm) and minimal (0.4 mm) radius. The bubble, formed in a 37° C., water-enclosed, 20-μl sample chamber, is monitored through a microscopic optic while the pressure changes are recorded on a strip chart recorder calibrated for 0 and −2 cm $H_2O$.

Determination of Composite Hydrophobicity Value

The composite hydrophobicity value of each peptide was determined by assigning to each amino acid residue in a peptide its corresponding hydrophilicity value as described in Table 1 of Hopp, et al, *PNAS USA* 78: 3824–3829 (1981), which disclosure is incorporated herein by reference. For a given peptide, the hydrophilicity values were summed, the sum representing the composite hydrophobicity value.

Preparation of Surfactants

After admixture with solvent, each peptide was combined with phospholipids (DPPC:PG), 3:1 to form a surfactant according to one of the following methods.

Method A was accomplished by admixing 16 μl of peptide/solvent admixture (40 μg peptide) with 100 μl of chloroform containing 400 μg phospholipids, agitating the admixture for about 10 at 37° C. to form a peptide/phospholipid admixture. Chloroform was removed from the peptide/phospholipid admixture by drying under $N_2$. The surfactant thus formed was then admixed with 90 μl of $H_2O$ and gently agitated for about 10 minutes at 37° C. Subsequently, 10 μl of 9% NaCl was admixed to the surfactant-containing solution.

Method B was accomplished by first placing 100 μl of chloroform containing 400 μg of phospholipids in a glass tube and removing the chloroform by drying under $N_2$ for about 10 minutes at 37° C. Sixteen μl of peptide/solvent admixture and 74 μl $H_2O$ were admixed with the dried phospholipids, and then gently agitated for about 10 minutes at 37° C. To the surfactant thus formed was admixed 10 μl of 9% NaCl. 15 Method C was accomplished by first maintaining the polypeptide-PL admixture at 43° C. for 10 minutes, after which time the solvents were removed from the admixture by drying under $N_2$. When needed, admixtures were further dried by 15 minutes exposure to vacuum to form a dried polypeptide-PL admixture. Water was then admixed with each dried admixture in an amount calculated to equal 90% of the volume necessary to give a final PL concentration of either 5 or 10 mg/ml (as indicated in Table 6) to form a second admixture. This second admixture was maintained for one hour at 43° C. with agitation. Subsequently, a volume of 6% NaCl equal to 10% of the volume necessary to give the desired PL concentration was admixed with the second admixture and the resulting final admixture was maintained for 10 minutes at 43° C. In most cases, the final admixture was subjected to a last step of 3 cycles of freezing and thawing.

Results

The surfactants illustrated in Table 5 were prepared as indicated in the table.

TABLE 5

| (1) Peptide/SEQ ID NO | Solvent | (2) Admixture Formed | (3) Phospholipid Admixture Method | (4) Composite Hydrophobicity Value |
|---|---|---|---|---|
| p1–15/12 | n-propyl alcohol | suspension | A | −16.7 |
| p11–25/12 | $H_2O$ | solution | B | +1.7 |
| p21–35/12 | Chloroform | suspension | A | −9.2 |
| p31–45/12 | $H_2O$ | solution | B | −9.9 |
| p41–55/12 | $H_2O$ | solution | B | −5.4 |
| p51–65/12 | $H_2O$ | suspension | B | −2.2 |
| p61–75/12 | methanol | suspension | A | −9.9 |
| p71–81/12 | $H_2O$ | suspension | B | +3.9 |

TABLE 5-continued

| (1) Peptide/SEQ ID NO | Solvent | (2) Admixture Formed | (3) Phospholipid Admixture Method | (4) Composite Hydrophobicity Value |
|---|---|---|---|---|
| p74–81/12 | H₂O | solution | B | +3.7 |
| p66–81/12 | methanol:H₂O | suspension | A | −1.0 |
| p52–81/12 | methanol:H₂O | suspension | A | −6.2 |

(1) All the identified peptides have an amino acid residue sequence corresponding to a portion of SEQ ID NO 12; for example, peptide p1–15 comprises amino acid residue nos. 1–15 of SEQ ID NO 12.
(2) Each polypeptide was admixed with the indicated solvent to achieve a concentration of 2.5 μg of peptide per μl of solvent.
(3) The letters indicate the surfactant preparation method used. Those methods are described above.
(4) The composite hydrophobicity value of each peptide was determined as described above.

Each of the surfactants identified in Table 5 was assayed for surfactant activity as evidenced by their ability to reduce surface tension in vitro using the "bubble assay" of Enhorning as described above.

The results of this study (data not shown) indicate that a subject polypeptide, when admixed with pharmaceutically acceptable phospholipids, forms a pulmonary surfactant that has greater surfactant activity than the phospholipids alone, as evidenced by the lower ΔP values. Typically 10% to 80% lower ΔP values were obtained using the polypeptides. It should be noted that the eight amino acid residue control peptide p74–81, which does not conform to the teachings of the present invention, did not form a PS having a greater activity than the phospholipid alone, thus indicating that amino acid residue length is a critical feature.

The surfactant activity of additional exemplary polypeptides of this invention was studied using the "bubble assay" as described above. The results of the study are illustrated below in Table 6.

Each polypeptide was admixed with the indicated solvent at a concentration of 2.5 mg of polypeptide per ml of solvent. The resulting admixture was observed to determine whether a solution or a suspension of insoluble polypeptide was formed. Those admixtures forming a suspension were further admixed by water bath sonication for 10 seconds to form a very fine suspension, sufficient for pipetting using glass pipettes.

After admixture with solvent, each peptide was admixed with phospholipids (PL), DPPC:PG, 3:1, in chloroform in a glass tube so that the amount of polypeptide added equaled one-tenth (10% by. weight) of the amount of PL added, to form a surfactant according to either method A, B or C.

Each of the surfactants was then assayed for surfactant activity as evidenced by their ability to reduce surface tension in vitro in the bubble assay performed as described above. The pressure gradient (ΔP) is a measure of surfactant activity in the polypeptide-PL third admixture which was determined using an Enhorning Surfactometer as described above. Measurements were obtained at time points of 15 seconds (15"), 1 minute (1') and 5 minutes (5') and are expressed as a mean of three independent measurements of the indicated polypeptide-PL admixture. Pressure gradient measurements for comparable samples of PL alone (PL) and natural human surfactants were determined as controls. The results of this study are shown in Table 6.

TABLE 6

| Peptide[1] | (2) Solvent | (3) Admixture Formed | Phospholipid Admixture Method | (4) Conc. of PL mg/ml | (5) Pressure Gradient 15" | 1' | 5' |
|---|---|---|---|---|---|---|---|
| p1–15 | N-propanol | suspension | A | 4 | 0.94 | 0.82 | 0.48 |
| p36–81 | 50% chloroform 0% methanol | suspension | C+ | 10 | 0.90 | 0.87 | 0.79 |
| p46–76 | 64% chloroform 36% methanol | solution | C+ | 10 | 0.90 | 0.80 | 0.62 |
| p51–72 | 75% chloroform 25% methanol | suspension | C+ | 10 | 1.15 | 0.76 | 0.33 |
| p51–76 | 37% chloroform 63% methanol | solution | C+ | 10 | 0.99 | 0.91 | 0.42 |
| p51–80 | 45% chloroform 55% methanol | solution | C+ | 10 | 0.92 | 0.89 | 0.48 |
| p51–81 | 50% chloroform 50% methanol | suspension | C+ | 10 | 0.94 | 0.86 | 0.64 |
| p52–81 | 67% DMF 33% chloroform | solution | A | 4 | 1.33 | 1.19 | 0.96 |
| p54–72 | 76% chloroform 24% methanol | suspension | C+ | 10 | 1.28 | 0.92 | 0.38 |
| p54–76 | 71% chloroform 24% methanol | suspension | C+ | 10 | 0.92 | 0.82 | 0.23 |
| p59–81 | 68% chloroform 32% methanol | solution | C− | 4 | 1.08 | 1.02 | 0.75 |
| p66–81 | 40% DMF 60% chloroform | suspension | A | 4 | 1.22 | 1.11 | 0.84 |
| p74–81 | water | solution | B | 4 | 2.37 | 2.32 | 2.31 |
| DL4 (31 mer) | 47% chloroform 53% methanol | solution | C− | 4 | 2.00 | 1.80 | 1.30 |
| RL4 | 32% chloroform 68% methanol | solution | C− | 4 | 0.58 | 0.65 | 0.33 |
| RL8 | 19% chloroform 81% methanol | suspension | C+ | 10 | 0.68 | 0.69 | 0.19 |

TABLE 6-continued

| Peptide[1] | Solvent | (2) Admixture Formed | (3) Phospholipid Admixture Method | (4) Conc. of PL mg/ml | (5) Pressure Gradient | | |
|---|---|---|---|---|---|---|---|
| | | | | | 15" | 1' | 5' |
| RL7 | 49% chloroform 51% methanol | solution | C– | 4 | 1.65 | 1.25 | 1.00 |
| RCL-1 | 79% chloroform 21% methanol | suspension | C+ | 10 | 0.50 | 0.59 | 0.06 |
| RCL-2 | 67% chloroform 33% methanol | suspension | C+ | 10 | 0.00 | 0.00 | 0.00 |
| RCL-3 | 75% chloroform 25% methanol | suspension | C+ | 10 | 0.55 | 0.51 | 0.33 |
| PL | | | C+ | 10 | >2.50 | >2.50 | 2.33 |
| Natural Human Surfactant | | | | 10 | 1.06 | 0.89 | 0.79 |

[1] All the identified peptides have an amino acid residue sequence corresponding to a portion of SEQ ID NO 12; for example, peptide p1–15 comprises amino acid residue nos. 1–15 of SEQ ID NO 12.
(2) Whether the initial admixture of peptide was a solution or a suspension is indicated.
(3) The letters indicate the surfactant preparation method used. Those methods are described above. A "+" indicates that the final admixture was subjected to a last step of 3 cycles of freezing and thawing. A "–" indicates the step was not performed.
(4) Concentration ("Conc.") of phospholipid (PL) in the final third admixture is indicated in milligrams PL per milliliter admixture (mg/ml).
(5) The pressure gradient is a measure of surfactant activity in the polypeptide-PL final admixture as determined using an Enhorning Surfactometer as described in Example 3. Measurements were obtained at three points of 15 seconds (15"), 1 minute (1') and 5 minutes (5') and are expressed as a mean of 3 independent measurements of the indicated polypeptide-PL admixture. Pressure gradient measurements for comparable samples of PL alone (PL) and natural human surfactant are also shown.

These results indicate that a subject polypeptide, when admixed with pharmaceutically acceptable phospholipids, forms a pulmonary surfactant that has a greater surfactant activity than the phospholipids alone, as demonstrated by the lower surface pressures obtained.

Example 4

In Vivo Assessment of Surfactant Activity

Preparation of Surfactants

A subject polypeptide was first admixed with solvent as described in Example 3. The resulting admixture was further admixed with phospholipid (PL) so that the amount of polypeptide added was either 3%, 7% or 10% by weight of the amount of PL added as indicated below. The final polypeptide, PL admixture (surfactant) was formed according to method C using the final freeze thaw step as described in detail in the "Preparation of Surfactants" section in Example 3, except that the final admixture had a concentration of 20 mg phospholipid per ml of final admixture.

Instillation Protocols.

Protocol 1

Fetal rabbits were treated by injection into the trachea of a 0.1 ml solution that contained either a synthetic surfactant prepared in Example 4A or either 2 mg of native surfactant prepared as described in Example 1 of U.S. Pat. No. 5,260,273 (incorporated by reference herein) or 2 mg PL.

Protocol 2

Surfactant was instilled in rabbit fetal lung by injection into the trachea from a single syringe of the following three components such that the components exit the syringe in the following order: (1) 0.05 ml air; (2) 0.1 ml of a synthetic surfactant prepared in Example 4A or either 2 mg of PL or 2 mg of native surfactant; and (3) 0.1 ml air.

Protocol 3

From one syringe, a 0.1 ml aliquot of synthetic surfactant prepared in Example 4A (or 2 mg of NS or of PL), was instilled into the rabbit trachea as described above, followed by injection of 0.05 ml lactated Ringer's Solution and 0.2 ml air from a second syringe.

Protocol 4

From one syringe, 0.1 ml of a synthetic surfactant prepared as described in Example 4A (or 2 mg of NS or of PL), 0.15 ml air, 0.1 ml saline, and 0.3 ml air were injected into the trachea as described above. Two subsequent aliquots of 0.3 ml air were given.

Protocol 5

Fetal rabbits were treated by injection into the trachea from a single syringe the following four components such that the four components exit the syringe upon injection in the order listed: (1) 0.2 ml solution that contains either a synthetic surfactant prepared in Example 4A or either 4 mg of native surfactant, or 4 mg PL; (2) a 0.15 ml volume of air; (3) a 0.1 ml normal saline solution; and (4) a 0.3 ml volume of air. The above injection was then repeated 15 minutes after the first injection.

Protocol 6

Rabbits were treated as described in Protocol 5, except that two subsequent aliquots of 0.3 ml air were given following the initial instillation and no additional instillation was given at 15 min.

Fetal Rabbit Model for Studying Surfactant Activity

The surfactant activity of exemplary polypeptides of this invention was studied using the methods described in detail previously by Revak, et al, *Am. Rev. Respir. Dis.* 134: 1258–1256 (1986), with the exceptions noted hereinbelow.

Twenty-seven day gestation fetal rabbits were delivered by hysterotomy and immediately injected with 0.05 ml Norcuron (Organon, Inc., N.J.) to prevent spontaneous breathing. The fetal rabbits were then weighed and a small cannula was inserted into the trachea by tracheotomy surfactant prepared as described above was then instilled into the fetal rabbit lung by one of the above instillation protocols.

Following instillation the rabbit was placed in a specially designed plethysmograph (containing a Celesco transducer) connected to a ventilator (Baby Bird, Baby Bird Corp., Palm Springs, Calif.) and the instilled lung was ventilated at a rate of 30 cycles per minute with a peak inspiratory pressure of 25 cm $H_2O$, a positive end expiratory pressure of 4 cm $H_2O$ and an inspiratory time of 0.5 seconds. In some studies, dynamic compliance measurements were made at various times throughout the ventilation procedure. In others, static compliance measurements were made following ventilation.

Static compliance measurements were made after 30 minutes of ventilation. The animals were removed from the ventilator and the lungs were degassed at −20 cm $H_2O$ in a bell jar under vacuum. Thereafter, the lungs were first inflated and then deflated through a T-connector attached to a tracheostomy tube. The volume of air required to reach static pressures of 5, 10, 15, 20, 25 and 30 cm $H_2O$ was measured during both inflation and deflation phases to generate static pressure to volume curves as a measure of static compliance.

Using the plethysmograph, dynamic compliance measurements were made at various times throughout a 60 minute ventilation period. Computer-assisted data analysis resulted in compliance data expressed as ml of air per cm $H_2O$ per gram of body weight at each time point. Compliance was calculated by the formula below.

$$\text{Compliance} = \frac{\Delta V}{\Delta P}$$

$\Delta P_{tp} = (C)^{-1} \cdot (\Delta V) + (R) \cdot (F)$ $P_{tp}$=transpulmonary pressure C=compliance (elastic component—relates change in volume to pressure)

R=resistance (relates flow to pressure)

F=flow

V=volume=the integral of flow with respect to time

The above equation was solved with a multiple linear regression for C and R. The compliance (C) represents the elastic nature of the lungs and the resistance (R) represents the pressure necessary to overcome the resistance to the flow of gas into and out of the lungs.

Results

Static compliance data using instillation protocols 1 and 5 are shown in FIGS. 2 and 3, respectively. Improved lung compliance was seen in all lungs treated with natural surfactant or with the surfactants of the present invention tested as compared with those lungs treated with phospholipids (PL) alone, with one exception. The surfactant prepared using p1–15 (FIGS. 3A and 3B) did not produce improved lung compliance over PL alone when measured by static compliance.

The results of the dynamic compliance studies are illustrated in Table 7.

TABLE 7

| | | Dynamic Compliance in ml air/cm $H_2O$ (g body weight × $10^6$) | | | | | | |
|---|---|---|---|---|---|---|---|---|
| | % Peptide Compound | Minutes after Surfactant instillation | | | | | | Sample[1] Given By |
| | To PL | 10 | 20 | 30 | 40 | 50 | 60 | Protocol # |
| PL | | 7 | 8 | 7 | 10 | 11 | 15 | 4 |
| | | 24 | 22 | 23 | 23 | 22 | 20 | 4 |
| | | 15 | 16 | 17 | 18 | 21 | 29 | 4 |
| NS | | 265 | 251 | 168 | 186 | 173 | 147* | 4 |
| | | 418 | 388 | 405 | 288 | 237 | * | 4 |
| | | 155 | 176 | 172 | | 172 | 179 | 4 |
| p36–81 | 5% | | | 255 | | | 146* | 3 |
| | 5% | | | 245 | | | 291 | 3 |
| | 10% | | | 154 | | | 1,162 | 2 |
| | 10% | | | 252 | | | 623 | 2 |
| p52–81 | 5% | | | 517 | | | 226* | 3 |
| | 5% | | | 434 | | | 55* | 3 |
| | 10% | | | 195 | | | 1,243 | 2 |
| | 10% | | | 43 | | | 1,690 | 2 |
| p51–76 | 10% | 33 | 22 | 56 | 87 | 124 | 85 | 4 |
| | 10% | 10 | 11 | 186 | 358 | 141 | 144* | 4 |
| | 10% | 15 | 36 | 109 | 241 | 264 | 301 | 4 |
| p51–80 | 10% | 17 | 41 | 52 | 78 | 99 | 208 | 4 |
| | 10% | 76 | 94 | 149 | 149 | 217 | 308 | 4 |
| | 10% | 23 | 71 | 130 | 156 | 182 | 109* | 4 |

[1]Prior to instillation into the rabbits, these samples were filtered through a 25 micron filter.
*A decrease in compliance with time may indicate the development of pneumothorax.

As shown in Table 7, each of the surfactants of this invention and natural surfactant improved dynamic compliance values in comparison to phospholipid alone.

Figures 1, 5A:
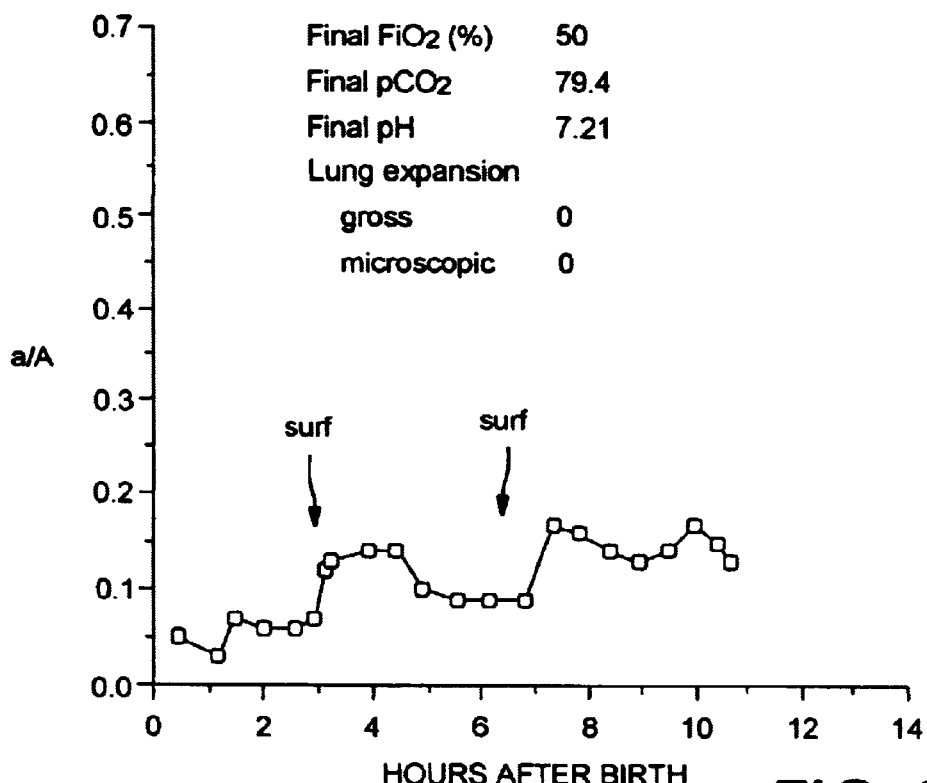
FIGS. 5A and 5B illustrate the effect of administration of $KL_4$-containing surfactant on lung function.
Figures 2, 5A:
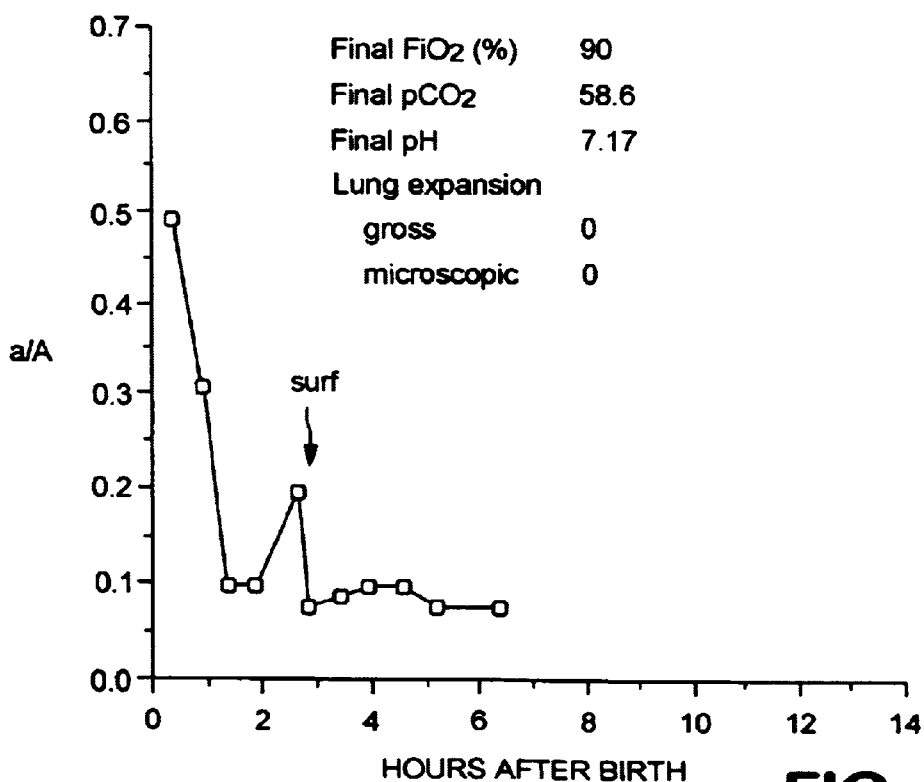
Figures 3, 5A:
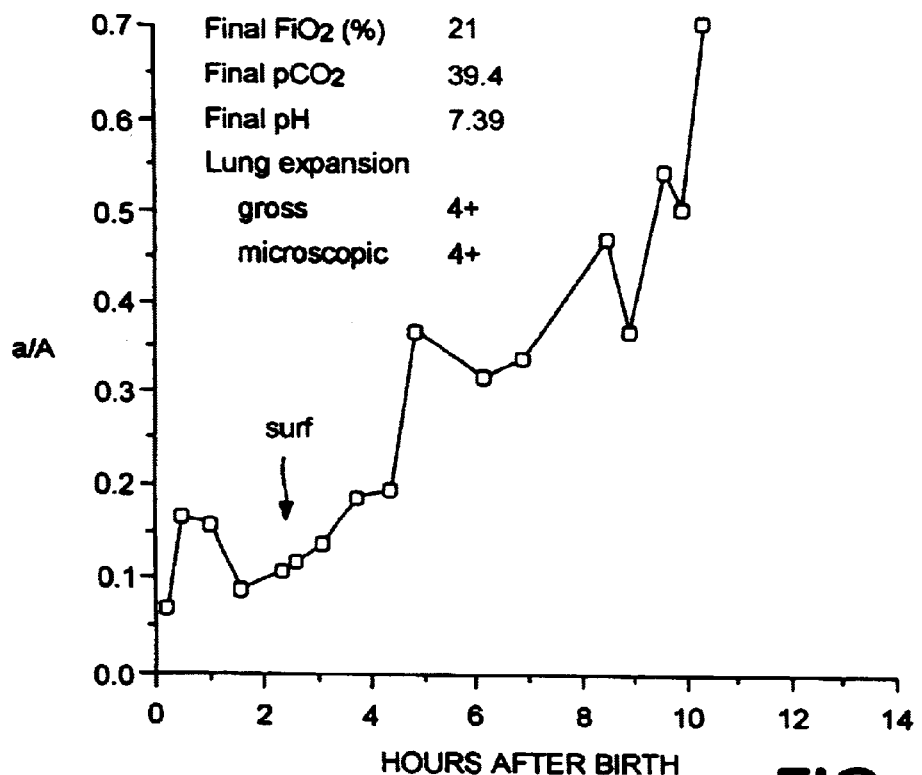
Figures 4, 5A:
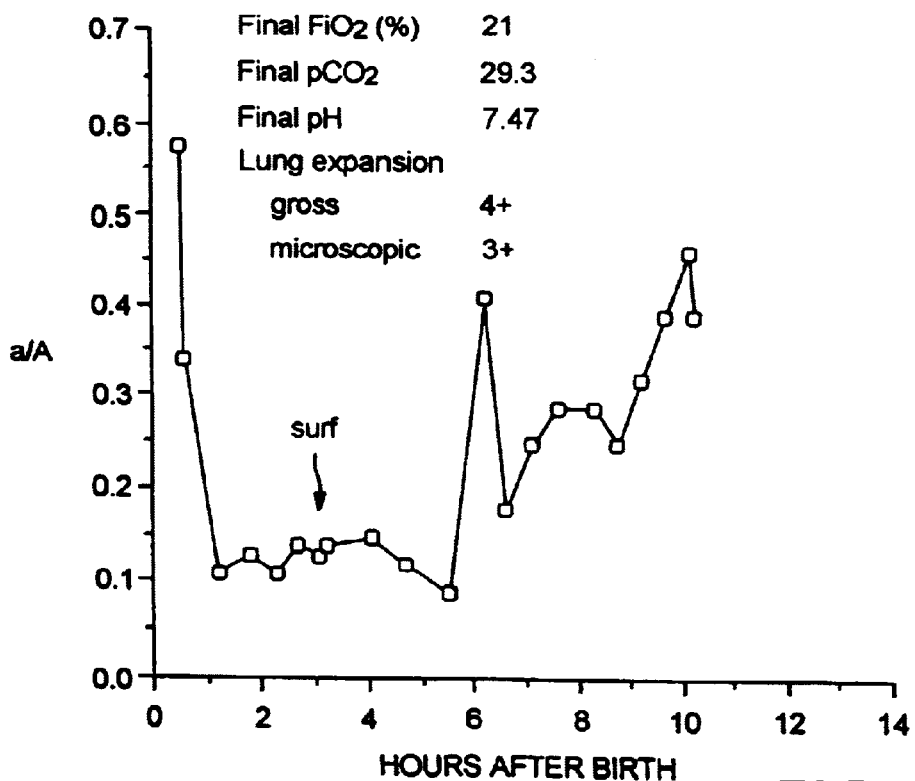
FIG. 4 illustrates a 750 nucleotide cDNA sequence (top lines; SEQ ID NO 11) and deduced amino acid residue sequence (bottom lines; SEQ ID NO 12). The number to the right of each line of nucleotides represents the numerical position in the sequence of the nucleotide at the end of each line. The nucleotides are grouped into codons, 15 codons per line, with the amino acid residue coded for by each codon shown in triple letter code directly below the codon. The numerical position of some residues in the amino acid residue sequence encoded by the cDNA is shown below the residues. The amino-terminal amino acid residue of mature human SP18 monomer is Phe (encoded by nucleotides 187–189) and is designated residues number 1. The carboxy-terminal amino acid residue is Asp at residue position 81 (encoded by nucleotides 427–429). A structural gene encoding mature SP18 monomer therefore contains 81 codons and has a nucleotide sequence that corresponds to nucleotides 187–429.
Figures 1, 5B:
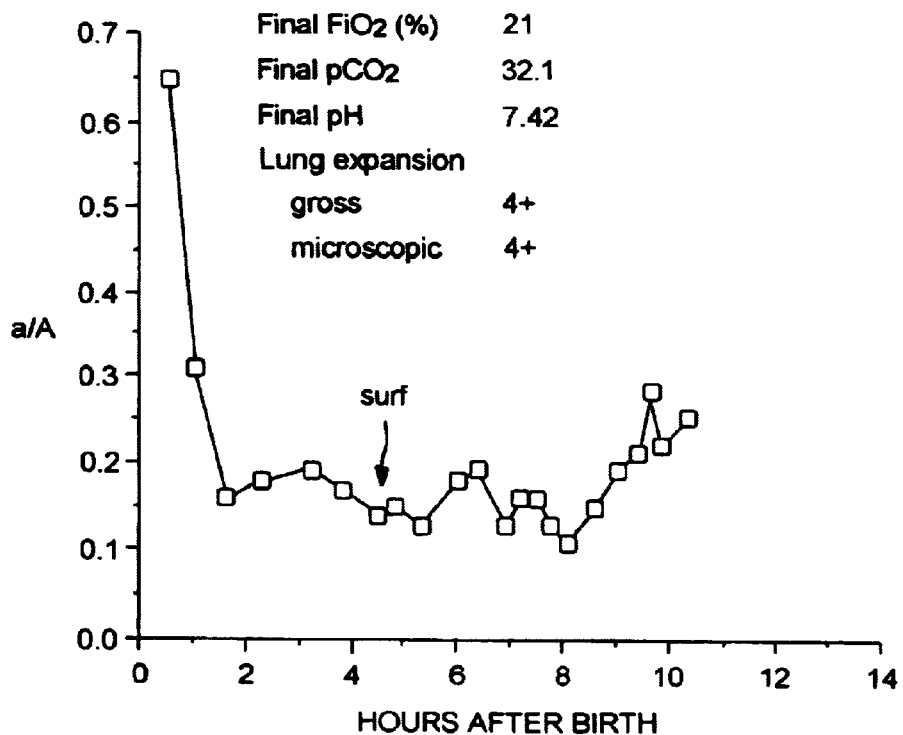
Figures 2, 5B:
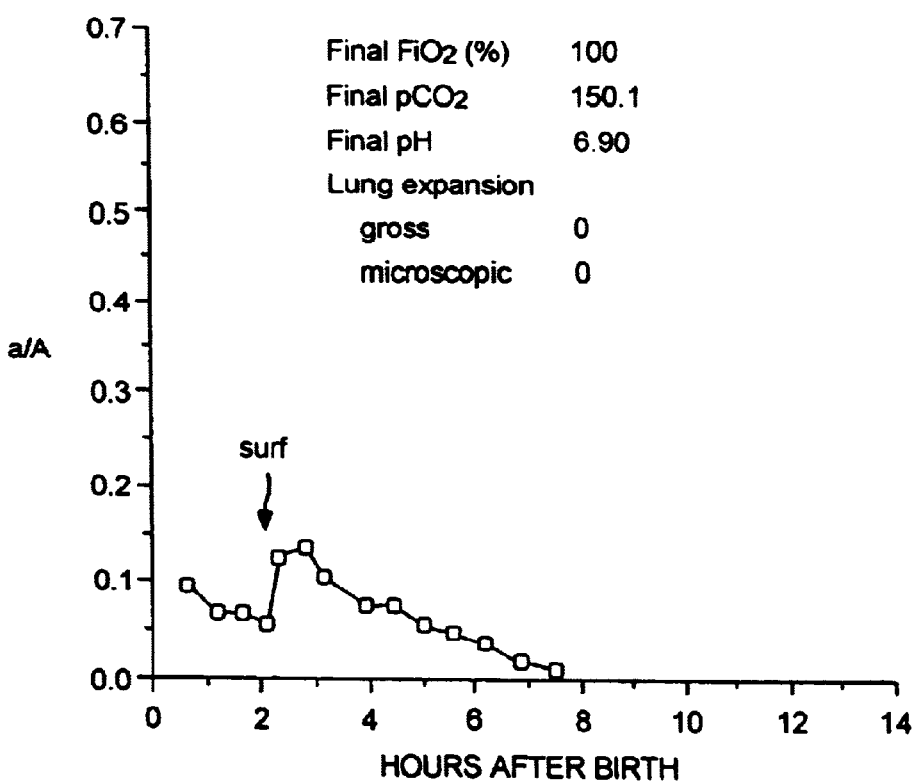
Figures 3, 5B:
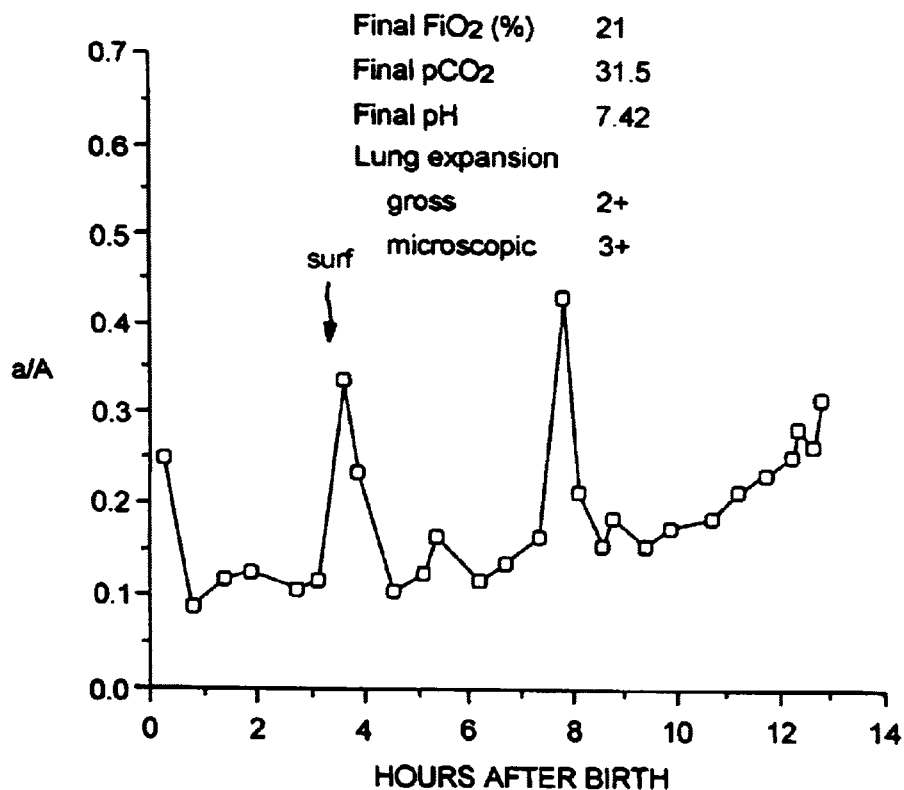
Figures 4, 5B:
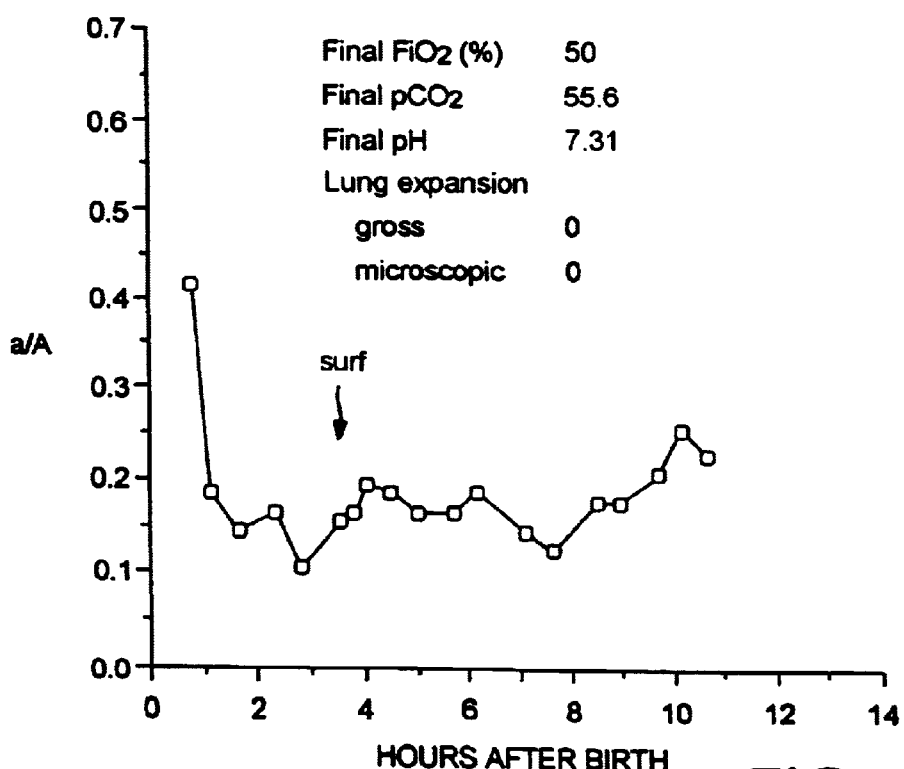

In addition, FIGS. 5A and 5B illustrate the effect of administration of $KL_4$-containing surfactant on lung function in primates. In FIGS. 5A and 5B, the data for eight monkeys are shown; four received $KL_4$-containing surfactant, while four received another surfactant (i.e., one not containing a surfactant peptide of the present invention). As an index of oxygenation, a/A (arterial/alveolar) $O_2$ ratios were calculated at the time of each measurement of arterial $pO_2$. These values, along with radiographic evidence and clinical assessment of the monkeys' condition, allowed a determination of the presence and severity of RDS. (An a/A ratio of 0.2–0.4 confirms the presence of RDS; values below 0.2 indicate severe RDS.) Further details of the primate studies are available in published PCT application No. WO 92/22315, the disclosures of which are incorporated herein by reference.

Discussion

The in vivo compliance studies demonstrate that the use of a number of exemplary surfactants of this invention resulted in enhanced compliance in comparison to phospholipid alone for each of the assayed surfactants. Thus, the proteins and polypeptides of this invention when admixed with pharmaceutically acceptable phospholipids form surfactants that have greater surfactant activity than phospholipid alone. Use of the surfactants is advantageous in producing improved compliance values in vivo.

The foregoing specification, including the specific embodiments and examples, is intended to be illustrative of the present invention and is not to be taken as limiting. Numerous other variations and modifications can be effected without departing from the true spirit and scope of the present invention.

We claim:

1. A polypeptide comprising at least 10 amino acid residues and no more than 60 amino acid residues, said polypeptide represented by the formula $(Z_a J_b)_c Z_d$, wherein:

Z is an amino acid residue independently selected from the group consisting of R, D, E, and K;

J is an α-aminoaliphatic carboxylic acid selected from the group consisting of α-aminobutanoic acid, α-aminopentanoic acid, α-amino-2-methylpropanoic acid and α-aminohexanoic acid;

a is 1 to 5;

b is 3 to 20;

c is 1 to 10;

d is 0 to 3, and wherein said polypeptide, when admixed with a pharmaceutically acceptable phospholipid, forms a pulmonary surfactant having a surfactant activity greater than the surfactant activity of the phospholipid alone.

2. A compound to claim 1 wherein said phospholipid is present in the range of 50–100 weight percent, in a polypeptide:phospholipid weight ratio in the range of 1:7 to 1:1,000.

3. A compound according to claim 1 wherein said phospholipid is selected from the group consisting of:

1,2-dipalmitoyl-sn-glycero-3-phosphocholine (dipalmitoylphosphatidylcholine, DPPC);

phosphatidyl glycerol (PG); and an admixture of DPPC and PG in a weight ratio of about 3:1.

4. A compound according to claim 1 further comprising palmitic acid, wherein said phospholipid comprises 50–90 weight percent and said palmitic acid comprises the remaining 10–50 weight percent of the lipid portion of said surfactant.

5. A liposomal surfactant composition prepared from a polypeptide comprising at least 10 amino acid residues and no more than 60 amino acid residues, said polypeptide including a sequence having alternating groupings of amino acid residues represented by the formula $(Z_a J_b)_c Z_d$, wherein:

Z is an amino acid residue independently selected from the group consisting of R, D, E, and K;

J is an α-aminoaliphatic carboxylic acid selected from the group consisting of α-aminobutanoic acid, α-aminopentanoic acid, α-amino-2-methylpropanoic acid and α-aminohexanoic acid;

is 1 to 5;

b is 3 to 20;

c is 1 to 10; and d is 0 to 3.

* * * * *

UNITED STATES PATENT AND TRADEMARK OFFICE
CERTIFICATE OF CORRECTION

PATENT NO. : 6,613,734 B2
DATED : September 2, 2003
INVENTOR(S) : Charles G. Cochrane and Susan D. Revak It is certified that error appears in the above-identified patent and that said Letters Patent is hereby corrected as shown below:

<u>Title page, Item [54] and Column 1, line 1,</u>
Title, should read as follows:
-- PEPTIDE-CONTAINING LIPOSOMAL SURFACTANTS --

<u>Column 41,</u>
Line 44, Claim 2 should read as follows:
2. A compound according to claim 1 wherein said phospholipid is present in the range of 50-100 weight percent, in a polypeptide:phospholipid weight ratio in the range of 1:7 to 1:1,000.

Signed and Sealed this

Twentieth Day of January, 2004

JON W. DUDAS
*Acting Director of the United States Patent and Trademark Office*